(12) United States Patent
Feldman et al.

(10) Patent No.: US 11,918,355 B2
(45) Date of Patent: Mar. 5, 2024

(54) ANALYTE SENSORS AND SENSING METHODS FOR THE DETECTION OF ALCOHOL

(71) Applicant: ABBOTT DIABETES CARE INC., Alameda, CA (US)

(72) Inventors: Benjamin J. Feldman, Berkeley, CA (US); Tianmei Ouyang, Alameda, CA (US); Ahmed Hisham Wali, Alameda, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 99 days.

(21) Appl. No.: 17/005,755

(22) Filed: Aug. 28, 2020

(65) Prior Publication Data
US 2021/0059587 A1  Mar. 4, 2021

Related U.S. Application Data

(60) Provisional application No. 62/894,306, filed on Aug. 30, 2019.

(51) Int. Cl.
*A61B 5/1486* (2006.01)
*G01N 33/98* (2006.01)

(52) U.S. Cl.
CPC ......... *A61B 5/14865* (2013.01); *G01N 33/98* (2013.01)

(58) Field of Classification Search
CPC ............... A61B 5/14865; G01N 33/98; G01N 27/3271; G01N 27/3272; C12Q 1/001; C12Q 1/002; C12Q 1/003; C12Q 1/004; C12Q 1/005; C12Q 1/25; C12Q 1/26; C12Q 1/32
See application file for complete search history.

(56) References Cited

U.S. PATENT DOCUMENTS

| | | | |
|---|---|---|---|
| 6,134,461 | A | 10/2000 | Say et al. |
| 6,605,200 | B1 | 8/2003 | Mao |
| 6,736,957 | B1 | 5/2004 | Forrow |
| 7,501,053 | B2 | 3/2009 | Karinka |
| 7,754,093 | B2 | 7/2010 | Forrow |
| 8,983,568 | B2 | 3/2015 | Bommakanti et al. |
| 10,136,816 | B2 | 11/2018 | Bernstein et al. |
| 11,230,727 | B2 * | 1/2022 | Buck .................. C12Q 1/004 |
| 2012/0276565 | A1 * | 11/2012 | Roedel ........... C12Y 101/01001 435/14 |
| 2016/0313358 | A1 * | 10/2016 | Titmus ................. B01L 3/5023 |
| 2019/0004005 | A1 | 1/2019 | Oja |

(Continued)

OTHER PUBLICATIONS

ISR-WO from related matter PCT/US2020/048497 dated Nov. 19, 2020.

*Primary Examiner* — Puya Agahi
*Assistant Examiner* — Grace L Rozanski
(74) *Attorney, Agent, or Firm* — Sterne, Kessler, Goldstein & Fox P.L.L.C.

(57) ABSTRACT

Apparatus, methods, and systems for detecting alcohol concentrations of an individual, and in particular in vivo alcohol concentrations of an individual. Alcohol sensing compositions include at least one alcohol-responsive active area comprising a concerted enzyme system having at least a first enzyme and second enzyme capable of acting in concert to facilitate the detection of alcohol. At least one of the enzymes in the concerted enzyme system is a ketoreductase.

16 Claims, 20 Drawing Sheets

(56) References Cited

U.S. PATENT DOCUMENTS

| | | |
|---|---|---|
| 2019/0024130 A1 | 1/2019 | Ouyang |
| 2019/0233869 A1* | 8/2019 | Devadoss ................ C12Q 1/26 |
| 2019/0357827 A1* | 11/2019 | Li ........................ A61B 5/6866 |
| 2019/0382819 A1* | 12/2019 | Mischler ................ C12Q 1/006 |
| 2022/0025424 A1* | 1/2022 | Tapper .................. C12P 13/005 |

* cited by examiner

ANALYTE SENSORS AND SENSING METHODS FOR THE DETECTION OF ALCOHOL

CROSS REFERENCE TO RELATED APPLICATIONS

The present application claims the benefit of priority of U.S. Provisional Application 62/894,306 entitled "Analyte Sensors and Sensing Methods for the Detection of Alcohol," filed on Aug. 30, 2019, the entirety of which is incorporated herein by reference.

BACKGROUND

The detection of various analytes within an individual can sometimes be vital for monitoring the condition of their health and well-being. Deviation from normal analyte levels can often be indicative of an underlying physiological condition, such as a metabolic condition or illness, or exposure to particular environmental factors or stimuli.

Analyte monitoring in an individual may take place periodically or continuously over a period of time. Periodic analyte monitoring may take place by withdrawing a sample of bodily fluid, such as blood, at one or more time intervals and analyzing ex vivo. Continuous analyte monitoring may be conducted using one or more sensors that remain at least partially implanted within a tissue of an individual, such as dermally, subcutaneously, or intravenously so that analyses may be conducted in vivo. Implanted sensors may collect analyte data at any dictated rate, depending on an individual's particular health needs and/or previously measured analyte levels, for example.

Any analyte may be suitable for analysis in vivo provided that a suitable chemistry can be identified for sensing the analyte. Indeed, in vivo amperometric sensors configured for assaying glucose have been developed and refined over recent years. Other analytes commonly subject to physiological dysregulation that may similarly be desirable to monitor include, but are not limited to, lactate, oxygen, pH, A1c, ketones, drug levels, and the like.

Another analyte that may be of particular importance to the medical wellbeing of an individual is alcohol level. Indeed, information pertaining to the in vivo alcohol levels of an individual may be used to predict or monitor the level of another analyte of interest. For example, alcohol may alter the glycemic control of an individual, whose glucose levels are naturally dysregulated or otherwise lack homeostasis without intervention, which may be detrimental to the individual. Other analytes that may be dysregulated by alcohol include, among others, triglycerides (e.g., related to heart disease, stroke, blood pressure, obesity), gamma-glutamyl transferase (GGT) (e.g., related to cancer, hepatitis, bone disease), and cortisol (e.g., related to stress, inflammation). Accordingly, it is desirable to monitor an alcohol level in an individual.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

FIGS. 12A-12B compare ADH to KRT A15 Linearity.

FIG. 13 compares ADH and KRT A15 beaker stability.

DETAILED DESCRIPTION

Figure 1:
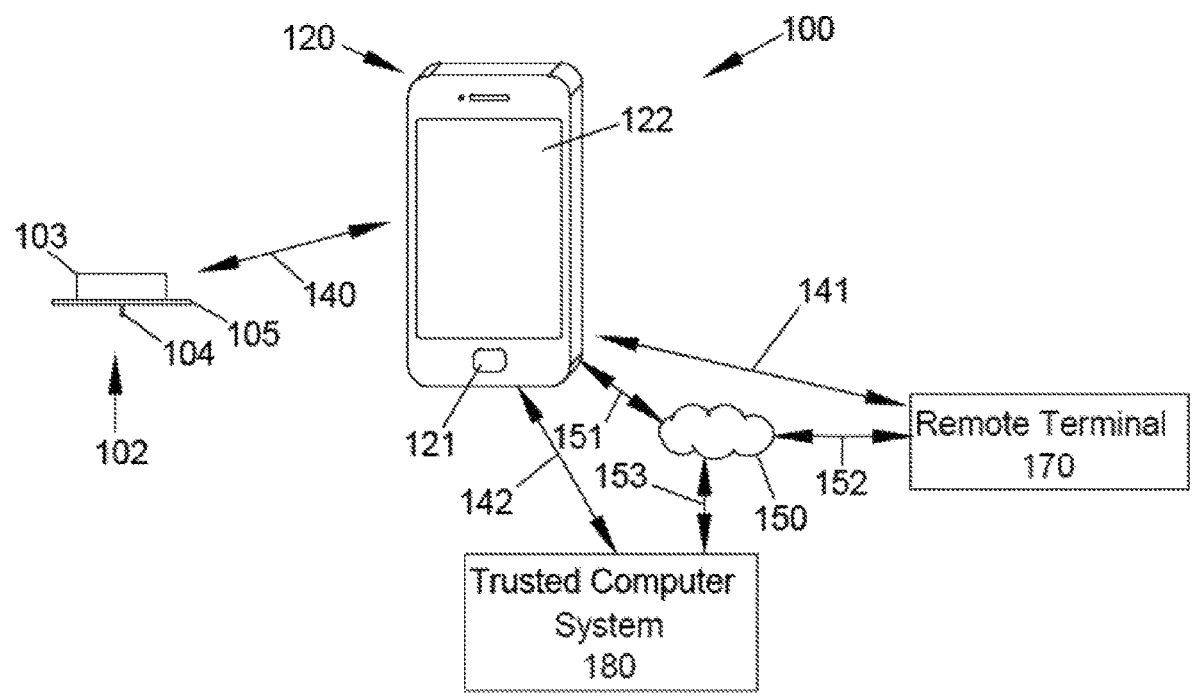
FIG. 1 shows a diagram of an illustrative sensing system that may incorporate an analyte sensor of the present disclosure.

The present disclosure generally describes analyte sensors and methods employing enzymes for the detection of in vivo alcohol levels.

Analyte sensors are commonly used to detect various analytes, typically employing an enzyme having particular specificity for a particular substrate. For example, glucose-responsive analyte sensors represent a well-studied and still-evolving field to aid diabetic individuals in better managing their health. However, other in vivo analytes are additionally of import and may be of great value in determining and/or monitoring the health of an individual, including determining and/or monitoring the influence of the analyte of interest on the dysregulation of other analytes.

In vivo alcohol concentrations of an individual may change dramatically based on alcohol consumption, poisoning, and/or based on various physiological factors. For example, individuals vary as to their ability to metabolize alcohol, thus causing alcohol levels to vary between individuals consuming the same dose of alcohol per body weight. Indeed, the equilibrium concentration of alcohol in a tissue depends on at least water content, rate of blood flow, and the mass of the tissue. Alcohol is able to pass through biological membranes and, thus, alcohol can readily flow from the bloodstream to all tissues and fluids, and said flow is proportional to the water content of the tissues and fluids. Further, in rare instances, an individual may produce quantities of alcohol through endogenous fermentation within the digestive system without alcohol consumption. As described above, the presence of certain concentrations of alcohol may additionally influence the function of one or more other analytes of an individual, further influencing the health of an individual.

Current alcohol measurements are performed by taking physical blood samples, urine samples, saliva samples, or the use of breath tests. However, such measurements are static in time and, in some instances, may be beset with false positive or false negative results and thus at least occasionally inaccurate. Differently, the present disclosure provides analyte sensors that are responsive to alcohol over time to promote health management. As used herein, the term "alcohol," and grammatical variants thereof, refers to any primary, secondary, or tertiary alcohol. For example, the alcohol sensors of the present disclosure may detect ethanol, methanol, butanol, propanol, isopropyl alcohol, and the like, and any combination thereof.

The alcohol sensors described herein are responsive to in vivo alcohol levels and are capable of providing "continuous" measurement of said alcohol levels. That is, the alcohol sensors described herein may be operable to provide a plurality of alcohol concentration measurements over an extended (continuous) period of time, such as seconds, minutes, or hours to days, weeks, or months.

The alcohol sensors may provide a number of advantages for monitoring dynamic levels of alcohol associated with resultant physiological conditions and effects on other analytes of interest. For example, the sensors of the present disclosure utilize specialized enzymatic reactions including one or more ketoreductases (referred to herein as "KRT").

The KRT-comprising sensing chemistry described herein advantageously overcomes various hurdles associated with typical detection of alcohol levels in an individual, including overcoming enzyme inhibition due to one or more products of the enzymatic reaction of the sensing chemistry, as discussed in greater detail herein below. By overcoming enzyme inhibition, the alcohol sensors of the present disclosure, among other things, may permit use of a single mass-limiting membrane and the manufacture of more cost-efficient sensors requiring less complicated sensing area configurations, without compromising effectiveness. The KRT-comprising chemistry is further advantageously receptive to both primary and secondary alcohols, including a particularly unexpected affinity toward secondary alcohol detection.

An individual wearing the continuous alcohol sensors described herein may access real-time alcohol level information to make various decisions based thereon, such as whether it is safe to drive, whether their glucose or other analyte levels are likely dysregulated based on the alcohol level and thus require action, and the like, and any combination thereof. Moreover, the alcohol sensors of the present disclosure may be used to monitor, test for, and/or evaluate alcohol levels in individuals suffering from alcohol misuse, abuse, or addiction. In doing so, the health of such individuals may be monitored by the individuals themselves, or by health practitioners or law enforcement professionals. Sensor electronics and processing algorithms associated with operating the sensors and sensing system described herein, including display units or devices thereof, may also provide direction, guidance, recommendations, and/or output concerning alcohol concentrations and suggested actions based thereon. Suitable processing algorithms, processors, memory, electronic components, and the like may reside in any of a trusted computer system, remote terminal, cloud server, reader device, and/or a housing for the sensor itself. Guidance, recommendations, output, and/or the like may be shown upon a suitable display unit or device that is in electronic communication with one or more of these components. The display unit or device may be a dedicated reader device or a personal communication device, such as a mobile phone (e.g., an iPhone® or Android device). Alternately, the display unit or device may be a third-party server, cloud server, or remote terminal that communicates with various software- and healthcare-related applications, such as a personal health monitor. Suitable remote terminals, cloud servers, or the like may further relay an output to associated secondary devices such as smart home devices, wearable technology, personal health monitors, or the like, or combinations thereof.

The present disclosure further describes sensing systems incorporating one or more alcohol sensors. The systems may include various sensing components, such as a processor and/or coding instructions (algorithms) therein, that are adapted to process sensor data received from the alcohol sensor and determine one or a plurality of alcohol concentrations therefrom. The processor and/or coding instructions may, in some embodiments, then analyze the alcohol concentration to determine one or more recommendations based on the particular alcohol concentration. For example, the alcohol concentration or other quantity derivable from the alcohol concentration at a particular evaluation time may be used to suggest whether another health analyte may be influenced negatively. In such case, the processor and/or coding instructions may suggest various ways in which an individual may react based on the alcohol concentration detected, including immediate and future action suggestions.

For example, depending on an individual's specific alcohol concentration, a recommendation may be whether or not to operate a motor vehicle, whether to perform an action to compensate for another analyte affected (e.g., if the analyte is glucose, whether to consume a carbohydrate or inject insulin), whether to seek medical attention, and the like, and any combination thereof.

Before describing the alcohol sensors of the present disclosure in more detail, a brief overview of suitable in vivo analyte sensor configurations and sensor systems employing the analyte sensors will first be provided so that the embodiments of the present disclosure may be better understood. It is to be understood that any of the sensor systems and analyte sensor configurations described hereinafter may feature one or more enzymes used to detect alcohol, and generally to detect alcohol in vivo, in accordance with the various embodiments of the present disclosure.

FIG. 1 shows a diagram of an illustrative sensing system that may incorporate an alcohol sensor of the present disclosure. As shown, sensing system 100 includes sensor control device 102 and reader device 120 that are configured to communicate with one another over a local communication path or link, which may be wired or wireless, uni- or bi-directional, and encrypted or non-encrypted. Reader device 120 may constitute an output medium for viewing analyte concentrations and alerts or notifications determined by sensor 104 or a processor associated therewith, as well as allowing for one or more user inputs, according to some embodiments. Reader device 120 may be a multi-purpose smartphone or a dedicated electronic reader instrument. While only one reader device 120 is shown, multiple reader devices 120 may be present in certain instances. Reader device 120 may also be in communication with remote terminal 170 and/or trusted computer system 180 via communication path(s)/link(s) 141 and/or 142, respectively, which also may be wired or wireless, uni- or bi-directional, and encrypted or non-encrypted. Reader device 120 may also or alternately be in communication with network 150 (e.g., a mobile telephone network, the internet, or a cloud server) via communication path/link 151. Network 150 may be further communicatively coupled to remote terminal 170 via communication path/link 152 and/or trusted computer system 180 via communication path/link 153. Alternately or additionally, sensor 104 may communicate directly with remote terminal 170 and/or trusted computer systems 180 without an intervening reader device 120 being present. For example, sensor 104 may communicate with remote terminal 170 and/or trusted computer system 180 through a direct communication link to network 150, according to some embodiments, as described in U.S. Patent Application Publication 2011/0213225 and incorporated herein by reference in its entirety.

Any suitable electronic communication protocol may be used for each of the communication paths or links, such as near field communication (NFC), radio frequency identification (RFID), BLUETOOTH® or BLUETOOTH® Low Energy protocols, WiFi, or the like. Remote terminal 170 and/or trusted computer system 180 may be accessible, according to some embodiments, by individuals other than a primary user who have an interest in the user's alcohol levels. Reader device 120 may comprise display 122 and optional input component 121. Display 122 may comprise a touch-screen interface for outputting information related to the sensor control device and inputting information by a user, for example.

Sensor control device 102 includes sensor housing 103, which may house circuitry and a power source for operating sensor 104. Optionally, the power source and/or active circuitry may be omitted. A processor (not shown) may be communicatively coupled to sensor 104, with the processor being physically located within sensor housing 103 or reader device 120. Sensor 104 protrudes from the underside of sensor housing 103 and extends through adhesive layer 105, which is adapted for adhering sensor housing 103 to a tissue surface, such as skin, according to some embodiments.

Sensor 104 is adapted to be at least partially inserted into a tissue of interest, such as within the dermal or subcutaneous layer of the skin. Sensor 104 may comprise a sensor tail of sufficient length for insertion to a desired depth in a given tissue. The sensor tail may comprise at least one working electrode and one or more active areas (sensing regions/spots or sensing layers) located upon the at least one working electrode and that are active for sensing alcohol (or in some instances one or more additional analytes). In some embodiments, the active areas are in the form of one or more discrete spots (e.g., one to about 10 spots, or more), which may range in size from about 0.01 $mm^2$ to about 1 $mm^2$, encompassing any value and subset therebetween, although larger or smaller individual active area spots are also contemplated herein.

The one or more active areas may comprise one or more enzymes, according to one or more embodiments of the present disclosure, to at least facilitate the detection of alcohol. The active areas may include a polymeric material to which, in some embodiments, one or more (or all) of the enzymes are chemically bonded (e.g., covalently bonded, ionically bonded, and the like) or otherwise immobilized (e.g., unbound in a matrix), according to some embodiments. In some embodiments, each active area may be overcoated with a mass-limiting or bio-compatibility membrane and/or further comprise an electron transfer agent to facilitate detection of at least alcohol.

In various embodiments of the present disclosure, at least alcohol levels may be monitored in any biological fluid of interest such as dermal fluid, interstitial fluid, plasma, blood, lymph, synovial fluid, cerebrospinal fluid, saliva, bronchoalveolar lavage, amniotic fluid, or the like. In particular embodiments, analyte sensors of the present disclosure may be adapted for assaying dermal fluid or interstitial fluid to determine concentrations of alcohol in vivo.

With continued reference to FIG. 1, in some embodiments, sensor control unit 102 may automatically forward data obtained with sensor 104 to reader device 120. For example, alcohol concentration data may be communicated automatically and periodically, such as at a certain frequency as data is obtained or after a certain time period has passed, with the data being stored in a memory until transmittal (e.g., every several seconds, every minute, five minutes, or other predetermined time period). In other embodiments, sensor control unit 102 may communicate with reader device 120 in a non-automatic manner and not according to a set schedule. For example, data may be communicated from sensor control unit 102 using NFC or RFID technology when the sensor electronics are brought into communication range of reader device 120. Until communicated to reader device 120, data may remain stored in a memory of sensor control device 102. Thus, a patient does not have to maintain close proximity to reader device 120 at all times, and can instead upload data at a convenient time. In yet other embodiments, a combination of automatic and non-automatic data transfer may be implemented. For example, data transfer may continue on an automatic basis until reader device 120 is no longer in communication range of sensor control unit 102. While automatic and non-automatic data transfer from sensor control unit 102 has been described with reference to reader device 120, such transfer mechanisms are equally applicable to remote terminal 170 and/or trusted computer system 180, without departing from the scope of the present disclosure.

An introducer may be present transiently to promote introduction of sensor 104 into a tissue. In illustrative embodiments, the introducer may comprise a needle or similar sharp. It is to be recognized that other types of introducers, such as sheaths or blades, may be present in alternative embodiments. More specifically, the needle or other introducer may transiently reside in proximity to or concurrently with sensor 104 prior to tissue insertion and then be withdrawn afterward. While present, the needle or other introducer may facilitate insertion of sensor 104 into a tissue by opening an access pathway for sensor 104 to follow. For example, the needle may facilitate penetration of the epidermis as an access pathway to the dermis to allow implantation of sensor 104 to take place, according to one or more embodiments. After opening the access pathway, the needle or other introducer may be withdrawn so that it does not represent a sharps hazard. In illustrative embodiments, suitable needles may be solid or hollow, beveled or non-beveled, and/or circular or non-circular in cross-section. In more particular embodiments, suitable needles may be comparable in cross-sectional diameter and/or tip design to an acupuncture needle, which may have a cross-sectional diameter of about 150 micrometers to about 300 micrometers (e.g., about 250 micrometers). It is to be recognized, however, that suitable needles may have a larger or smaller cross-sectional diameter if needed for particular applications.

In some embodiments, a tip of the needle or introducer (while present) may be angled over the terminus of sensor 104, such that the needle or introducer penetrates a tissue first and opens an access pathway for sensor 104. In other illustrative embodiments, sensor 104 may reside within a lumen or groove of the needle or inserter, with the needle similarly opening an access pathway for sensor 104. In either case, the needle is subsequently withdrawn after facilitating sensor insertion.

The alcohol sensors disclosed herein may feature active areas located upon a single working electrode (e.g., on one or both sides of a single working electrode) or upon two or more separate working electrodes (e.g., on one or both sides of the two or more separate working electrodes). Single working electrode sensor configurations may employ two-electrode or three-electrode detection motifs, according to various embodiments of the present disclosure and as described further herein. Sensor configurations featuring a single working electrode are described hereinafter with reference to FIGS. 2A-2C. Each of these sensor configurations may suitably incorporate one or more alcohol-responsive active areas, according to various embodiments of the present disclosure. Sensor configurations featuring multiple working electrodes are described thereafter in reference to FIGS. 3 and 4. When multiple working electrodes are present, one or more alcohol-responsive active areas, one or more (or all) of the multiple working electrodes, or one of the working electrodes may be used to detect another analyte of interest in concert with detection of alcohol levels.

When a single working electrode is present in an alcohol sensor of the present disclosure, three-electrode detection motifs may comprise a working electrode, a counter electrode, and a reference electrode. Related two-electrode detection motifs may comprise a working electrode and a second electrode, in which the second electrode functions as one of a counter electrode or reference electrode, or as both a counter electrode and a reference electrode (i.e., a counter/reference electrode). In both two-electrode and three-electrode detection motifs, one or more active areas of the alcohol sensor may be in contact with the working electrode. The one or more active areas may comprise one or more enzymes according to the embodiments of the present disclosure. In some embodiments, the various electrodes may be at least partially stacked (layered) upon one another. In some or other embodiments, the various electrodes may be laterally spaced apart from one another upon the sensor tail. Similarly, the associated active areas upon each electrode may be stacked vertically upon top of one another or be laterally spaced apart. In either case, the various electrodes may be electrically isolated from one another by a dielectric material or similar insulator.

Figure 2A:
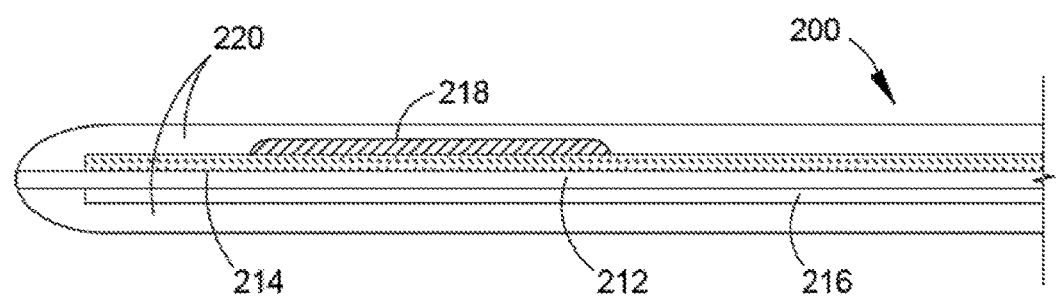
FIG. 2A shows a diagram of an illustrative two-electrode analyte sensor configuration having a single working electrode, which is compatible for use in some embodiments of the disclosure herein.

FIG. 2A shows a diagram of an illustrative two-electrode sensor configuration having a single working electrode, which is compatible for use in detecting alcohol according to embodiments of the present disclosure. As shown, sensor 200 comprises substrate 212 disposed between working electrode 214 and counter/reference electrode 216. Alternately, working electrode 214 and counter/reference electrode 216 may be located upon the same side of substrate 212 with a dielectric material interposed in between (configuration not shown). Active area 218 is disposed as at least one layer upon at least a portion of working electrode 214. In various embodiments, active area 218 may comprise multiple spots or a single spot configured for detection of one or more analytes of interest. Collectively, one or more enzymes may be present in active area 218 (i.e., in a single spot or in multiple spots).

Referring still to FIG. 2A, membrane 220 overcoats at least active area 218 and may optionally overcoat some or all of working electrode 214 and/or counter/reference electrode 216, or the entirety of analyte sensor 200, according to some embodiments. One or both faces of analyte sensor 200 may be overcoated with membrane 220. Membrane 220 may comprise one or more polymeric membrane materials having capabilities of limiting analyte flux to active area 218 and/or bio-compatibility capabilities. Sensor 200 may be operable for assaying at least alcohol by any of coulometric, amperometric, voltammetric, potentiometric electrochemical, or iontophoretic (including reverse iontophoresis) detection techniques.

Figure 2B:
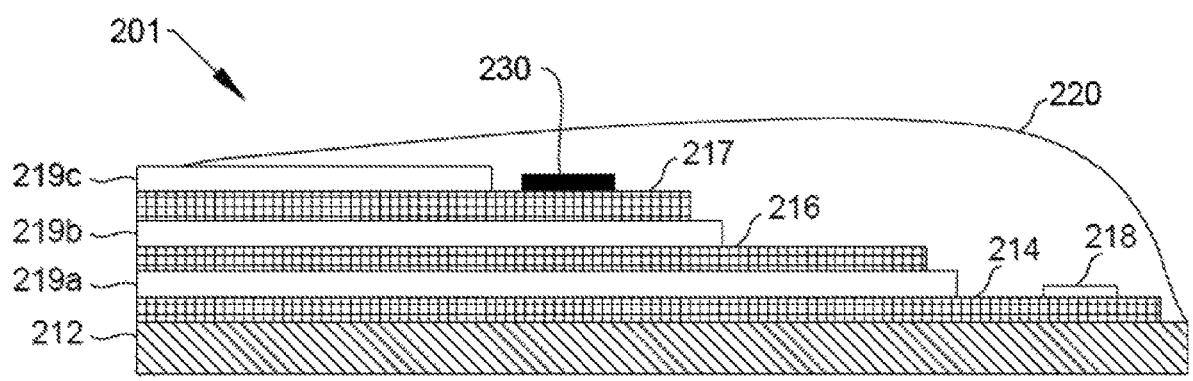
FIGS. 2B and 2C show diagrams of illustrative three-electrode analyte sensor configurations having a single working electrode, which are compatible for use in some embodiments of the disclosure herein.
Figure 2C:
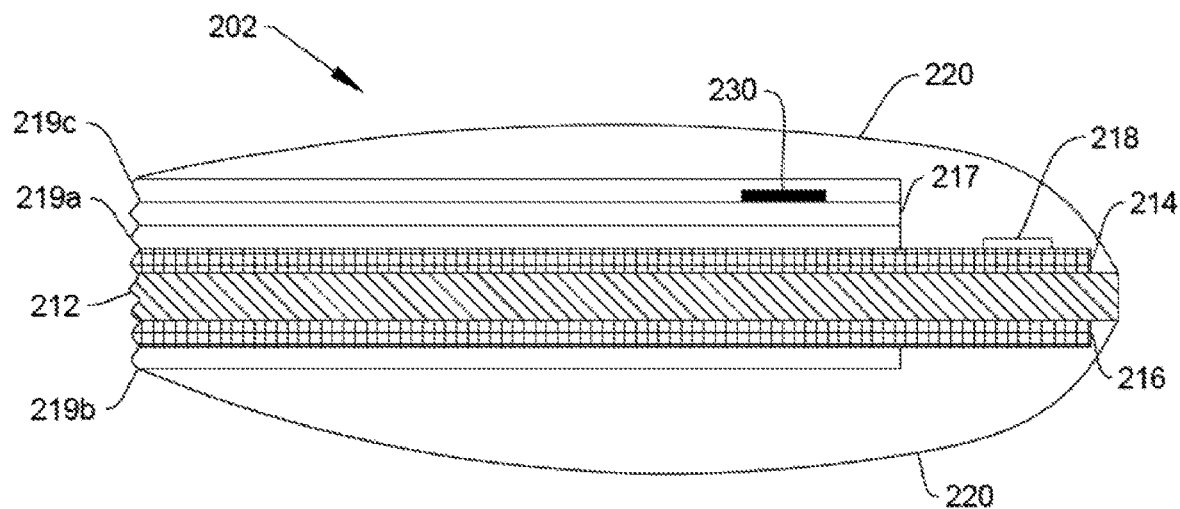

FIGS. 2B and 2C show diagrams of illustrative three-electrode analyte sensor configurations having a single working electrode, which are compatible for use in the embodiments of the present disclosure. Three-electrode analyte sensor configurations employing a single working electrode may be similar to that shown for sensor 200 in FIG. 2A, except for the inclusion of an additional electrode, represented as electrode 217 in sensors 201 and 202 (FIGS. 2B and 2C). With additional electrode 217, counter/reference electrode 216 may then function as either a counter electrode or a reference electrode, and additional electrode 217 fulfills the other electrode function not otherwise accounted for. Working electrode 214 continues to fulfill its original function. Additional electrode 217 may be disposed upon either working electrode 214 or electrode 216, with a separating layer of dielectric material in between. For example, as depicted in FIG. 2B, dielectric layers 219a, 219b, and 219c separate electrodes 214, 216, and 217 from one another to provide electrical isolation. Alternately, at least one of electrodes 214, 216, and 217 may be located upon opposite faces of substrate 212, as shown in FIG. 2C. Thus, in some embodiments, electrode 214 (working electrode) and electrode 216 (counter electrode) may be located upon opposite faces of substrate 212, with electrode 217 (reference electrode) being located upon one of electrodes 214 or 216 and spaced apart therefrom with a dielectric material. Alternatively, in some embodiments, electrode 214 (working electrode) and electrode 216 (reference electrode) may be located upon opposite faces of substrate 212, with electrode 217 (counter electrode) being located upon one of electrodes 214 or 216 and spaced apart therefrom with a dielectric material. In still other embodiments, the reference and counter electrode may be located on one face of the substrate 212 and the working electrode on the opposite face. Optionally, a reference material layer 230 (e.g., Ag/AgCl) may be present upon electrode 217, with the location of reference material layer 230 not being limited to that depicted in FIGS. 2B and 2C.

As with sensor 200 shown in FIG. 2A, active area 218 in analyte sensors 201 and 202 may comprise multiple spots or a single spot configured for detection of at least alcohol. Collectively, one or more enzymes may be present in active area 218 of sensors 201 and 202. Additionally, analyte sensors 201 and 202 may be operable for assaying at least alcohol by any of coulometric, amperometric, voltammetric, potentiometric electrochemical, or iontophoretic detection techniques.

With continued reference to FIGS. 2A and 2B, and like sensor 200, membrane 220 may also overcoat active area 218, as well as other sensor components, in sensors 201 and 202. Additional electrode 217 may be overcoated with membrane 220 in some embodiments. Although FIGS. 2B and 2C have depicted all of electrodes 214, 216, and 217 as being overcoated with membrane 220, it is to be understood that only working electrode 214 may be overcoated in some embodiments or only working electrode 214 and one other electrode may be overcoated in some embodiments. Moreover, the thickness of membrane 220 at each of electrodes 214, 216, and/or 217 may be the same or different, as well as the amount of surface area of each of electrodes 214, 216, and/or 217 that membrane 220 overcoats may be the same or different. As in two-electrode analyte sensor configurations (FIG. 2A), one or both faces of analyte sensors 201 and 202 may be overcoated with membrane 220 in the sensor configurations of FIGS. 2B and 2C, or the entirety of analyte sensors 201 and 202 may be overcoated. Accordingly, the three-electrode sensor configurations shown in FIGS. 2B and 2C should be understood as being non-limiting of the embodiments disclosed herein, with alternative electrode and/or layer configurations remaining within the scope of the present disclosure.

Figure 3:
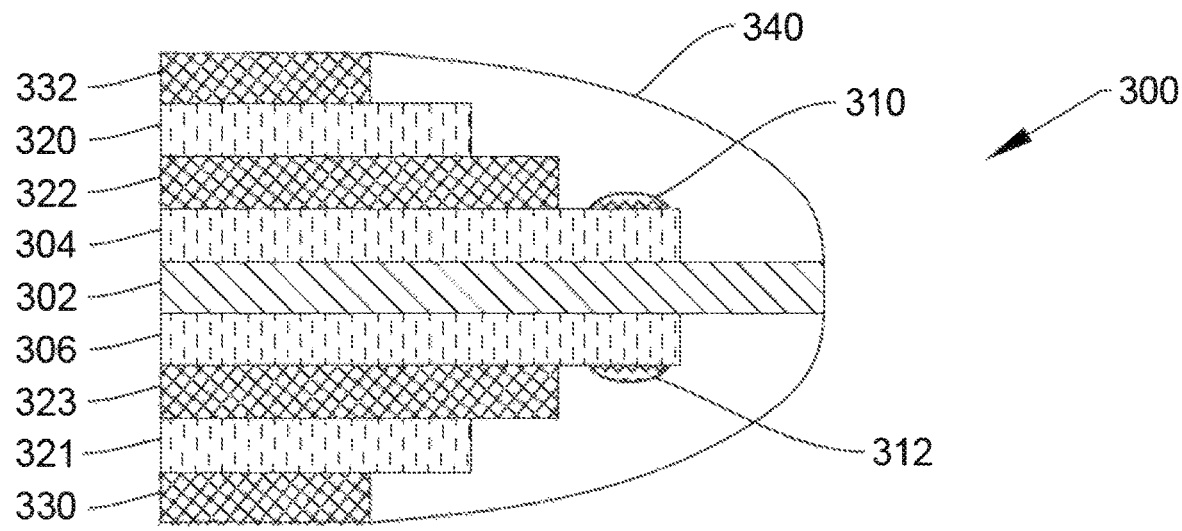
FIG. 3 shows a diagram of an illustrative analyte sensor configuration having two working electrodes, a reference electrode and a counter electrode, which is compatible for use in some embodiments of the disclosure herein.

FIG. 3 shows a diagram of an illustrative analyte sensor configuration having two working electrodes, a reference electrode and a counter electrode, which is compatible for use in an alcohol sensor described in the present disclosure. As shown in FIG. 3, sensor 300 includes working electrodes 304 and 306 disposed upon opposite faces of substrate 302. Active area 310 is disposed upon the surface of working electrode 304, and active area 312 is disposed upon the surface of working electrode 306. Collectively, one or more enzymes may be present in active areas 310 and 312 configured for at least the detection of alcohol. For example, active areas 310 and 312 may be both configured to detect alcohol concentrations. Alternatively, one of active area 310 or 312 may be configured to detect alcohol concentrations and the other active area configured to detect another analyte of interest (e.g., glucose, lactate, and the like). Counter electrode 320 is electrically isolated from working electrode 304 by dielectric layer 322, and reference electrode 321 is electrically isolated from working electrode 306 by dielectric layer 323. Outer dielectric layers 330 and 332 are positioned upon reference electrode 321 and counter electrode 320, respectively. Membrane 340 may overcoat at least active areas 310 and 312, according to various embodiments. Other components of analyte sensor 300 may be overcoated with membrane 340 as well, and as above, one or both faces of analyte sensor 300, or a portion thereof, may be overcoated with membrane 340. Like analyte sensors 200, 201, and 202, sensor 300 may be operable for assaying at least alcohol by any of coulometric, amperometric, voltammetric, potentiometric electrochemical, or iontophoretic detection techniques.

Alternative sensor configurations having multiple working electrodes and differing from that shown in FIG. 3 may feature a counter/reference electrode instead of separate counter and reference electrodes 320 and 321, and/or feature layer and/or membrane arrangements varying from those expressly depicted. For example, the positioning of counter electrode 320 and reference electrode 321 may be reversed from that depicted in FIG. 3. In addition, working electrodes 304 and 306 need not necessarily reside upon opposing faces of substrate 302 in the manner shown in FIG. 3.

Although the above description pertaining to FIGS. 2 and 3 is primarily directed to analyte sensor configurations having two working electrodes, it is to be appreciated that more than two working electrodes may be successfully incorporated through an extension of the disclosure herein. Additional working electrodes may allow additional active area(s) and corresponding sensing capabilities to be imparted to such sensors having such features.

Moreover, although FIGS. 2 and 3 show planar substrates (e.g., relatively flat) having electrically conductive structures (e.g., electrodes) and active areas disposed thereon, it is to be appreciated that an analyte sensor for use in the embodiments of the present disclosure may have various other configurations, without departing from the scope of the present disclosure. For example, the substrate may be substantially non-planar (e.g., relatively curved, semi-hemispherical, or spherical), cylindrical, helical, otherwise irregular in shape, and any combination thereof. Similarly, two or more electrodes may be substantially non-planar (e.g., relatively curved, semi-hemispherical, or spherical), cylindrical, helical, otherwise irregular in shape, and any combination thereof. The electrodes may be arranged in layers, concentrically, or otherwise, and typically isolated by one or more insulative regions. Sensing regions disposed on at least a working electrode may further cover at least a portion (or all) of a working electrode as a single layer or as discrete regions of various shapes, such as square, circular, semi-circular, arcuate, rectangular, polygonal, or otherwise irregular.

According to various embodiments of the present disclosure, an electron transfer agent may be present in one or more of the active areas of any of the alcohol sensors or alcohol sensor configurations disclosed herein. Suitable electron transfer agents may facilitate conveyance of electrons to the working electrode when an alcohol analyte (enzyme substrate) undergoes an oxidation-reduction reaction. Choice of the electron transfer agent within each active area may dictate the oxidation-reduction potential observed for the alcohol analyte.

Suitable electron transfer agents may include electro-reducible and electro-oxidizable ions, complexes or molecules (e.g., quinones) having oxidation-reduction potentials that are a few hundred millivolts above or below the oxidation-reduction potential of the standard calomel electrode (SCE). According to some embodiments, suitable electron transfer agents may include low-potential osmium complexes, such as those described in U.S. Pat. Nos. 6,134,461 and 6,605,200, which are incorporated herein by reference in their entirety. Additional examples include those described in U.S. Pat. Nos. 6,736,957; 7,501,053; and 7,754,093, the disclosures of each of which are incorporated herein by reference in their entirety. Other suitable electron transfer agents may comprise metal compounds or complexes of ruthenium, osmium, iron (e.g., polyvinylferrocene or hexacyanoferrate), cobalt, metallocene compounds thereof, and the like, for example. Suitable ligands for the metal complexes may also include, for example, bidentate or higher denticity ligands such as, for example, bipyridine, biimidazole, phenanthroline, or pyridyl(imidazole). Other suitable bidentate ligands may include, for example, amino acids, oxalic acid, acetylacetone, diaminoalkanes, or o-diaminoarenes. Any combination of monodentate, bidentate, tridentate, tetradentate, or higher denticity ligands may be present in a metal complex to achieve a full coordination sphere. In some embodiments, the selected electron transfer agent for use in the alcohol response active area(s) described herein is an osmium complex.

According to various embodiments of the present disclosure, one or more polymers may be present in each of the one or more active areas of any of the alcohol sensors or alcohol sensor configurations disclosed herein. For example, the enzymes may be each chemically bonded or otherwise immobilized in a single polymer. In other embodiments, such as when multiple enzymes are used, one or more enzymes may be polymerized to a first polymer and the one or more other enzymes polymerized to a second polymer, both polymers and enzymes forming an active area of an alcohol sensor.

Suitable polymers for inclusion in the active area(s) may include, but are not limited to, polyvinylpyridines (e.g., poly(4-vinylpyridine)), polyvinylimidazoles (e.g., poly(1-vinylimidazole)), any copolymer thereof, and any combination thereof. Illustrative copolymers that may be suitable for inclusion in the active areas include those containing monomer units such as styrene, acrylamide, methacrylamide, or acrylonitrile, for example. When multiple active areas are present, the one or more polymers within each active area may be the same or different. Any combination of the aforementioned polymers may also be used, without departing from the scope of the present disclosure.

According to various embodiments of the present disclosure, the electron transfer agent may be covalently bonded to one or more polymers in one or more of the active areas. The manner of covalent bonding is not considered to be particularly limited. Covalent bonding of the electron transfer agent to the one or more polymers may take place by polymerizing a monomer unit bearing a covalently bound electron transfer agent, or the electron transfer agent may be reacted with the one or more polymers separately after it has already been synthesized. According to some embodiments, a bifunctional spacer may covalently bond the electron transfer agent to the one or more polymers within the active area, with a first functional group being reactive with the one or more polymers (e.g., a functional group capable of quaternizing a pyridine nitrogen atom or an imidazole nitrogen atom) and a second functional group being reactive with the electron transfer agent (e.g., a functional group that is reactive with a ligand coordinating a metal ion).

In illustrative embodiments, one or more of the polymers within the active area(s) of the alcohol sensors disclosed herein may be a poly(4-vinylpyridine), in which a portion of the monomer units are functionalized with an alkylcarboxylate side chain, a portion of the monomer units are appended to an osmium electron transfer agent with an amido spacer group, and a portion of the monomer units are unfunctionalized. That is, the polymer may be a redox polymer of an osmium-decorated poly(vinylpyridine)-based polymer, referred to herein as "X7."

Similarly, according to some or other various embodiments of the present disclosure, the one or more enzymes within one or more of the active areas may be covalently bonded to the one or more polymers. When multiple enzymes are present in a single active area, all of the multiple enzymes may be covalently bonded to a single polymer or to two or more separate polymers, which may be the same or different. For example, if two or more enzymes are covalently bonded to separate, different polymers, one of the polymers may be coated upon the other to form the active area. In other embodiments, only a portion of the multiple enzymes may be covalently bonded to the one or more polymers. For example, a first enzyme may be covalently bonded to a first polymer and a second enzyme may be non-covalently associated with the first polymer or a second polymer.

Covalent bonding of an enzyme to a polymer may take place via a crosslinker introduced with a suitable crosslinking agent. Suitable crosslinking agents for reaction with free amino groups in the enzyme(s) may include crosslinking agents such as, for example, polyethylene glycol diglycidylether (PEGDGE) or other polyepoxides, cyanuric chloride, N-hydroxysuccinimide, imidoesters, epichlorohydrin, or derivatized variants thereof. Suitable crosslinking agents for reaction with free carboxylic acid groups in the enzyme may include, for example, carbodiimides. The crosslinking is generally intermolecular, but can be intramolecular in some embodiments.

As provided above, the electron transfer agent and/or the one or more enzymes may be associated with the one or more polymers in the active area(s) through means other than covalent bonding, as well. In some embodiments, the electron transfer agent and/or the one or more enzymes may be ionically or coordinatively associated with the one or more polymers. For example, a charged polymer may be ionically associated with an oppositely charged electron transfer agent or enzyme. In still other embodiments, the electron transfer agent and/or the one or more enzymes may be physically entrained within the one or more polymers without being bonded thereto.

In some embodiments, a stabilizer may be incorporated into the active area(s) of the alcohol sensors described herein to improve the functionality of the sensors and achieve desired sensitivity and stability. Such stabilizers may include an antioxidant and/or companion protein to stabilize the one or more enzymes, for instance. Examples of suitable stabilizers may include, but are not limited to serum albumin (e.g., humane or bovine serum albumin or other compatible albumin), a glutaraldehyde-crosslinked albumin, catalase, a glutaraldehyde-crosslinked catalase, other enzyme antioxidants, and the like, and any combination thereof. The stabilizers may be conjugated or non-conjugated, and chemically bound or unbound to the active area(s). The amount of stabilizer may vary depending upon the type of stabilizer selected, but may be in an amount of about 1% to about 50% by weight of a total active area (i.e., the weight of the combined components of an active area), encompassing any value and subset therebetween, such as about 1% to about 25%, or about 10% to about 25% by weight of a total active area.

In certain embodiments, the mass-limiting membrane or bio-compatibility membrane may be disposed upon at least a portion of an active area(s). Suitable membranes may be composed of crosslinked polymers containing heterocyclic nitrogen groups, such as polymers of polyvinylpyridine and/or polyvinylimidazole. Embodiments also include membranes that are made of a polyurethane, polyether urethane, or chemically related material, membranes that are made of silicone, and the like.

In some embodiments, a membrane may be formed by crosslinking in situ a polymer, including those discussed above, modified with a zwitterionic moiety, a non-pyridine copolymer component, and optionally another moiety that is either hydrophilic or hydrophobic, and/or has other desirable properties, in a buffer solution (e.g., an alcohol-buffer solution or other biological buffer solution, such as HEPES). The modified polymer may be made from a precursor polymer containing heterocyclic nitrogen groups. For example, a precursor polymer may be polyvinylpyridine and/or polyvinylimidazole. Optionally, hydrophilic or hydrophobic modifiers may be used to "fine-tune" the permeability of the resulting membrane to alcohol, or even a particular type of alcohol of interest. Optional hydrophilic modifiers, such as poly(ethylene glycol), hydroxyl or polyhydroxyl modifiers, and the like, and any combinations thereof, may be used to enhance the bio-compatibility of the resultant membrane.

The membrane may be applied over the active area(s) by placing a droplet or droplets of membrane solution on at least the one or more working electrodes of an alcohol sensor, such as by dipping the sensor tail into the membrane solution, by spraying the membrane solution on the sensor tail, by heat pressing or melting the membrane in any sized layer (such as discrete or all encompassing), vapor deposition of the membrane solution, powder coating of the membrane solution, and the like, and any combination thereof.

Generally, the thickness of the membrane is controlled by the concentration of the membrane solution, by the number of droplets of the membrane solution applied, by the number of times the sensor tail is dipped in the membrane solution, by the volume of membrane solution sprayed on the sensor tail, and the like, and by any combination of these factors. In some embodiments, the membrane described herein may have a thickness ranging from about 0.1 micrometers ($\mu m$) to about 1000 $\mu m$, encompassing any value and subset therebetween, such as from about 1 $\mu m$ to about 500 $\mu m$, or about 10 $\mu m$ to about 100 $\mu m$. As stated above, the membrane may overlay one or more active area(s), and in some embodiments, the active area(s) may have a thickness of from about 0.1 $\mu m$ to about 10 $\mu m$, encompassing any value and subset therebetween. Further, the active areas may range in size from about 0.001 $mm^2$ to about 1 $mm^2$, encompassing any value and subset therebetween. It is to be appreciated, however, that thicker or thinner membrane(s), thicker and thinner active area(s), and larger or smaller active area(s) are also contemplated herein.

In some embodiments, the membrane may comprise a compound including, but not limited to, poly(styrene-co-maleic anhydride), dodecylamine and poly(propylene glycol)-block-poly(ethylene glycol)-block-poly(propylene glycol) (2-aminopropyl ether) crosslinked with poly(propylene glycol)-block-poly(ethylene glycol)-block-poly(propylene glycol) bis(2-aminopropyl ether); poly(N-isopropyl acrylamide); a copolymer of poly(ethylene oxide) and poly (propylene oxide); polyvinylpyridine; a derivative of polyvinylpyridine; polyvinylimidazole; a derivative of polyvinylimidazole; and the like; and any combination thereof. In some embodiments, the membrane may be comprised of a polyvinylpyridine-co-styrene polymer, in which a portion of the pyridine nitrogen atoms are functionalized with a non-crosslinked poly(ethylene glycol) tail and a portion of the pyridine nitrogen atoms are functionalized with an alkylsulfonic acid group. Other membrane compounds, alone or in combination with any aforementioned membrane compounds, may comprise a suitable copolymer of 4-vinylpyridine and styrene and an amine-free polyether arm. Any combination of the aforementioned membrane polymers may also be used, without departing from the scope of the present disclosure.

The membrane compounds described herein may further be crosslinked with one or more crosslinking agents, including those listed above with reference to enzyme(s). For example, suitable crosslinking agents may include, but are not limited to, polyethylene glycol diglycidylether (PEGDGE), glycerol triglycidyl ether (Gly3), polydimethylsiloxane diglycidylether (PDMS-DGE), or other polyepoxides, cyanuric chloride, N-hydroxysuccinimide, imidoesters, epichlorohydrin, or derivatized variants thereof, and any combination thereof. Branched versions with similar terminal chemistry are also suitable for the present disclosure. For example, in some embodiments, Formula 1 may be crosslinking with triglycidyl glycerol ether and/or PEDGE and/or polydimethylsiloxane diglycidylether (PDMS-DGE).

In some embodiments, the membrane composition for use as a mass transport limiting layer of the present disclosure may comprise polydimethylsiloxane (PDMS), polydimethylsiloxane diglycidylether (PDMS-DGE), aminopropyl terminated polydimethylsiloxane, and the like, and any combination thereof for use as a leveling agent (e.g., for reducing the contact angle of the membrane composition or sensing element(s) composition). Branched versions with similar terminal chemistry are also suitable for the present disclosure. Certain leveling agents may additionally be included, such as those found, for example, in U.S. Pat. No. 8,983,568, the disclosure of which is incorporated by reference herein in its entirety.

In some instances, the membrane may form one or more bonds with the one or more elements of the active area(s). As used herein, the term "bonds," and grammatical variants thereof, refers to any type of an interaction between atoms or molecules that allows chemical compounds to form associations with each other, such as, but not limited to, covalent bonds, ionic bonds, dipole-dipole interactions, hydrogen bonds, London dispersion forces, and the like, and any combination thereof. For example, in situ polymerization of the membrane can form crosslinks between the one or more polymers of the membrane and the one or more polymers in the active area(s). In some embodiments, crosslinking of the membrane to the active area(s) facilitates a reduction in the occurrence of delamination of the membrane from the sensor.

As previously stated, the present disclosure provides various methods, systems, and apparatuses for the detection of at least an alcohol (e.g., an alcohol concentration or level) within the bodily fluid of an individual. The detection may be in vitro or in vivo utilizing the active area(s) sensing chemistry described herein to overcome one or more hurdles in the manufacture of a desirable alcohol sensor.

Alcohol may be detected using one or more enzymes, such as an alcohol oxidase. As a representative example, alcohol oxidase interacts with alcohol, generally a primary alcohol, to form acetaldehyde ($C_2H_4O$) and hydrogen peroxide ($H_2O_2$). Other primary and secondary alcohols react to form aldehydes with a corresponding higher or lower carbon content. Alcohol oxidase only catalyzes the forward conversion of alcohol into acetaldehyde and comprise a strongly bound flavin co-factor. Accordingly, in theory, alcohol oxidase may be used in an analyte sensor for the detection of alcohol by assaying either acetaldehyde or hydrogen peroxide products produced in the enzymatic reaction. There are two issues with this approach, however. First, both acetaldehyde and hydrogen peroxide are inhibitory to alcohol oxidase. Thus, if these compounds are not cleared from the sensor environment, the alcohol oxidase becomes inactive for promoting alcohol oxidation, thereby leaving the sensor non-functional for assaying alcohol. Moreover, if acetaldehyde and hydrogen peroxide become sequestered or undergo quenching with other agents (further complicating the sensing composition of an active area), there is no longer a species or enough species available for electrochemical detection. Second, alcohol oxidase does not freely exchange electrons with oxidation-reduction mediators, other than molecular oxygen. As such, electron transfer agents associated with a polymer in the active area of a sensor, such as an osmium and other transition metal complexes discussed herein, are ineffective for cycling alcohol oxidase from an inactive reduced state into an oxidized state that is reactive with an alcohol.

Alcohol dehydrogenases are another group of enzymes that facilitate the conversion of alcohol, generally a primary alcohol, to aldehydes or ketones. As a representative example, alcohol dehydrogenase interacts with ethanol in the presence of oxidized nicotinamide adenine dinucleotide ($NAD^+$) to form acetaldehyde ($C_2H_4O$) and reduced nicotinamide adenine dinucleotide (NADH). Other primary and secondary alcohols react to form aldehydes with a corresponding higher or lower carbon content. Different from alcohol oxidase, alcohol dehydrogenases do not only catalyze the forward conversion of alcohol to an aldehyde (generally referred to herein as acetaldehyde, although other aldehydes having higher or lower carbon content may be produced), but also perform the reaction reversibly. Further different from alcohol oxidase, alcohol dehydrogenases do not comprise a bound co-factor and thus require an exogenous co-factor to render the enzymes active for promoting alcohol oxidation. Moreover, the activity of alcohol dehydrogenase is controlled, at least in part, based on product inhibition by NADH and acetaldehyde (see FIG. 4). These characteristics have typically rendered alcohol dehydrogenase unfavorable for use in designing sensing chemistry for an alcohol sensor.

The embodiments of the present disclosure utilize an oxidoreductase scheme for the detection of alcohol levels using one or more analyte sensor embodiments of the present disclosure. More particularly, the sensing chemistry described in the present disclosure utilizes two enzymes interacting in concert with one another in at least one active area upon a working electrode, in which one of the enzymes is a KRT. As used herein, the term "concerted enzymes" or "concerted enzyme system," and grammatical variants thereof, refers to at least two enzymes capable of interacting in concert (jointly) with one another. KRT is a type of oxidoreductase having NADH-dependent or NAD(P)(H)-dependent catalytic activity and known primarily to be capable of reducing aldehydes and ketones. Typically, KRTs are relatively inefficient as alcohol dehydrogenases because they lack metal co-factors, which are used to hold and position alcohol groups by alcohol dehydrogenases. KRTs further typically prefer NAD(P)H over NADH. Accordingly, their effective use in the detection of an alcohol level of an individual was not considered favorable.

The embodiments of the present disclosure provide a concerted enzyme system suitable for use in the detection of alcohol, wherein the concerted enzyme system utilizes a KRT. The KRTs described for use in the sensing chemistry of the present disclosure for the detection of alcohol include wild type (naturally occurring) and non-naturally engineered peptide chains exhibiting KRT functionality. For example, the aldo-KRT family may be suitable for use in the embodiments of the present disclosure. Without being bound by theory, it is further believed that variations of one or more residues in the active site of a KRT may alter its reaction mechanism and, thus, its affinity to the detection of alcohol. That is, certain KRTs may be more effective at alcohol detection compared to others, depending on their chemical makeup.

More particularly, the concerted enzyme system described herein utilizes a KRT and a diphorase. In the sensor configurations of the present disclosure, a KRT may convert alcohol and oxidized $NAD^+$ or oxidized nicotinamide adenine dinucleotide phosphate ($NAD(P)^+$) into an aldehyde (e.g., acetaldehyde) and reduced NADH or reduced nicotinamide adenine dinucleotide phosphate (NAD(P)H), respectively. The aldehyde serves as the representative molecule indicative of the presence of alcohol. The NADH or NAD(P)H may undergo reduction under diaphorase mediation, with the electrons transferred during this process providing the basis for alcohol detection at one or more working electrodes.

Figure 4A:
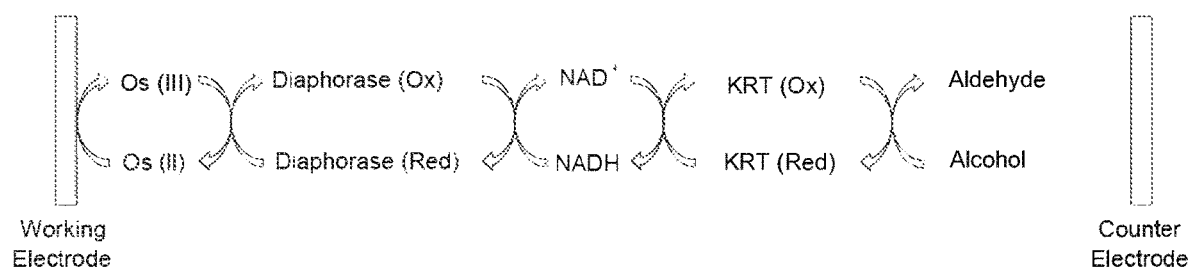
FIG. 4A shows a concerted enzyme system associated with alcohol detection using ketoreductase, nicotinamide adenine dinucleotide, and diaphorase located upon a working electrode, according to various embodiments of the present disclosure.
Figure 4B:
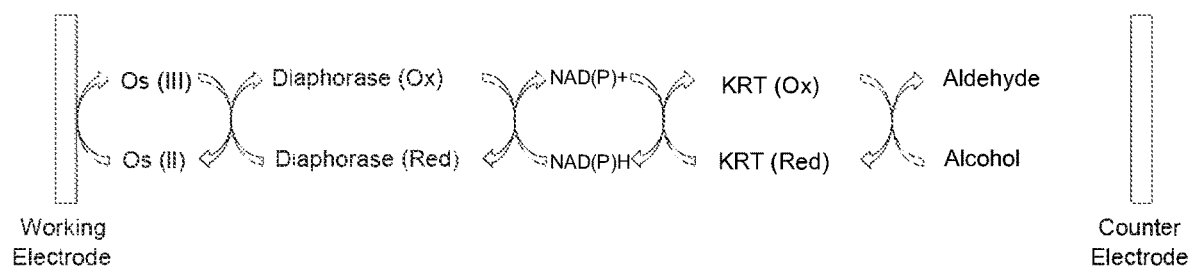
FIG. 4B shows a concerted enzyme system associated with alcohol detection using ketoreductase, nicotinamide adenine dinucleotide phosphate, and diaphorase located upon a working electrode, according to various embodiments of the present disclosure.

The concerted reaction between KRT and diaphorase, mediated by $NAD^+$ co-factor, for detection of alcohol is shown in FIG. 4A; the concerted reaction between KRT and diaphorase, mediated by $NAD(P)^+$ co-factor, for detection of alcohol is shown in FIG. 4B. In FIGS. 4A and 4B, diaphorase is chemically bonded (e.g., covalently) to a polymer that is disposed upon a working electrode (i.e., in an active area of an alcohol sensor) and KRT is chemically bound (e.g., covalently) to the same (e.g., via a crosslinker) or separate polymer. For example, in one embodiment, diaphorase may be chemically bound to a first polymer that is disposed upon a working electrode and KRT may be chemically bound to a second polymer that is disposed upon the first polymer. A membrane is disposed over the entirety of the active area and the particular co-factor (e.g., either $NAD^+$ or $NAD(P)^+$) may be non-covalently associated with a polymer in the active area, but otherwise membrane restricted. In addition to diaphorase and/or KRT, an osmium complex or other transition metal complex capable of exchanging electrons with the enzyme is also chemically (e.g., covalently) bonded to the polymer that is disposed upon the working electrode. For example, X7 comprises both covalently bound polymer and electron transfer agent, as described hereinabove. In some embodiments, the active area comprises X7 polymer, to which diaphorase and KRT are chemically bound, and are overcoated with a membrane.

Each of the KRT and diaphorase may be present in an amount in the range of about 1% to about 50% by weight of a total active area (i.e., the weight of the combined components of an active area), encompassing any value and subset therebetween, such as about 1% to about 40%, or about 10% to about 40% by weight of a total active area.

As can be appreciated from FIGS. 4A and 4B, the amount of enzymatically formed aldehyde (e.g., acetaldehyde) is proportional to the amount of alcohol. As such, the current produced at the working electrode during the KRT oxidation of the alcohol may be proportional to the amount of acetaldehyde present, and, by extension, the amount of alcohol present (i.e., an alcohol concentration or level). Correlation of the working electrode current to the alcohol concentration may take place by referring to a lookup table of currents at known alcohol concentrations or by utilizing a calibration curve.

Accordingly, in some embodiments, the present disclosure provides alcohol-responsive active area(s) based upon a concerted enzyme system of ketoreductase and diaphorase. More specifically, the present disclosure provides analyte sensors and systems comprising a sensor tail including at least a working electrode, and at least one alcohol-responsive active area disposed upon a surface of the working electrode, the alcohol-responsive active area comprising an enzyme system comprising at least two enzymes capable of acting in concert to facilitate the detection of alcohol, wherein one of the at least two enzymes is a ketoreductase. A membrane may further be overcoating the at least one alcohol-responsive active area. Additionally, at least the sensor tail of the analyte sensor may be configured for at least partial insertion into a tissue, such as dermally, subcutaneously, or intravenously so that analyses may be conducted in vivo. In other embodiments, the analyte sensor (including the sensor tail) may be wholly implanted within a tissue. Accordingly, the present disclosure provides a method of sensing alcohol using the analyte sensor described above. In particular, the at least one alcohol-responsive active area is exposed to a body fluid and during the duration of a user wearing the analyte sensor (e.g., one day or more, such as up to about one month or more), the active area may continuously assay for alcohol. A signal may be detected (e.g., by electrochemical detection) from the analyte sensor alcohol-responsive active area that is proportional to a concentration of alcohol.

Embodiments disclosed herein include:

Embodiment A: An analyte sensor comprising: a sensor tail comprising at least a working electrode; and at least one alcohol-responsive active area disposed upon a surface of the working electrode, the at least one alcohol-responsive active area comprising an enzyme system comprising at least a first enzyme and second enzyme capable of acting in concert to facilitate the detection of alcohol, wherein the first enzyme is a ketoreductase.

Embodiment B: A method comprising: detecting a signal proportional to a concentration of alcohol using an analyte sensor, the analyte sensor comprising: a sensor tail comprising at least a working electrode, the sensor tail configured for implantation into a tissue; and at least one alcohol-responsive active area disposed upon a surface of the working electrode, the at least one alcohol-responsive active area comprising an enzyme system comprising at least a first enzyme and second enzyme capable of acting in concert to facilitate the detection of alcohol, wherein the first enzyme is a ketoreductase.

Embodiment C: An electrode assembly comprising: at least one working electrode; and at least one alcohol-responsive active area disposed upon a surface of the at least one working electrode, the alcohol-responsive active area comprising an enzyme system comprising at least a first enzyme and second enzyme capable of acting in concert to facilitate the detection of alcohol, wherein the first enzyme is a ketoreductase.

Embodiment D: An alcohol sensing composition comprising: at least one alcohol-responsive active area comprising an enzyme system comprising at least a first enzyme and second enzyme capable of acting in concert to facilitate the detection of alcohol, wherein the first enzyme is a ketoreductase.

Embodiment E: A system comprising: an analyte sensor comprising: a sensor tail comprising at least a working electrode; and at least one alcohol-responsive active area disposed upon a surface of the working electrode, the at least one alcohol-responsive active area comprising an enzyme system comprising at least a first enzyme and second enzyme capable of acting in concert to facilitate the detection of alcohol, wherein the first enzyme is a ketoreductase; and a receiver configured for receiving a signal proportional to a concentration of alcohol from the analyte sensor.

Each of Embodiments A, B, C, D, and E may have one or more of the following additional elements in any combination:

Element 1: Wherein the second enzyme is diaphorase.

Element 2: Wherein the ketoreductase is an aldo-ketoreductase.

Element 3: Wherein the ketoreductase is KRED-P1-A04, KRED-P2-C11, KRED-P2-G03, or KRED-P2-H07 manufactured by Codexis®.

Element 4: Wherein a membrane is disposed upon the at least one alcohol-responsive active area.

Element 5: Wherein a membrane is disposed upon the at least one alcohol-responsive active area, and the membrane is one of a polyvinylpyridine, a polyvinylimidazone, or any copolymer thereof.

Element 6: Wherein the at least one alcohol-responsive active area comprises a polymer.

Element 7: Wherein the at least one alcohol-responsive active area comprises a polymer, and the first enzyme of ketoreductase and the second enzyme are chemically bound to the polymer.

Element 8: Wherein the at least one alcohol-responsive active area comprises an electron transfer agent.

Element 9: Wherein the at least one alcohol-responsive active area comprises a stabilizer.

By way of non-limiting example, exemplary combinations applicable to A, B, C, D, and E include:

Elements 1 and 2; 1 and 3; 1 and 4; 1 and 5; 1 and 6; 1 and 7; 1 and 8; 2 and 3; 2 and 4; 2 and 5; 2 and 6; 2 and 7; 2 and 8; 3 and 4; 3 and 5; 3 and 6; 3 and 7; 3 and 8; 4 and 5; 4 and 6; 4 and 7; 4 and 8; 5 and 6; 5 and 7; 5 and 8; 6 and 7; 6 and 8; 7 and 8; and any non-limiting combination of one, more than one, or all of 1, 2, 3, 4, 5, 6, 7, and 8.

To facilitate a better understanding of the embodiments described herein, including the advantages of the alcohol sensor as described above and as compared to other alcohol detection chemistry, the following examples of various representative embodiments are given. In no way should the following examples be read to limit, or to define, the scope of the invention.

Example 1

Example 1 evaluates the function of an alcohol sensor comprising a KRT using a two-layer active area system. Example 1 was used to screen 24 KRT candidates for use in an alcohol sensor.

Alcohol Sensor Preparation. Various experimental KRT comprising alcohol-responsive active areas were prepared using a two-layer active area system. The active area was coated onto a carbon working electrode (it is to be noted that other electrode surface types may be used in accordance with the embodiments of the present disclosure), wherein a first layer composition (Table 1 below) was initially coated directly upon the working electrode and a second layer composition (Table 2 below) was coated upon the first layer composition, the first and second layer comprising the active area. Following deposition of the first layer composition, the first layer composition was cured overnight at room temperature (RT) (approximately 25° C.); after curing of the first layer composition, the second layer composition was deposited and allowed to cure overnight at RT. Thereafter, a PVP membrane was applied to the working electrode using a coating solution formulated with 40:1 polyvinylpyridine-co-styrene(15) (i.e., having 15% styrene) and PEGDGE 400. The membrane was deposited over the active area (3×5 mm/second dipping) and allowed to cure overnight at RT, followed by 48 hours at 56° C. in desiccated vials. It is to be understood that the components of Table 1 and Table 2 may be applied in a single layer (i.e., a mixture of all of the components), with or without the additional crosslinker (PEGDGE 400) in Table 2, without departing from the scope of the present disclosure. The layered active area used in this Example was to facilitate ease of testing and comparison of a large number of KRT sensor samples.

TABLE 1

Example 1 First Active Area Layer Composition in 10 mM MES Buffer at pH = 5.5

| Component | Concentration (mg/mL) |
| --- | --- |
| Diaphorase | 10 |
| Albumin | 10 |
| X7 Polymer | 10 |
| PEGDGE 400 | 5 |

TABLE 2

Example 2 Second Active Area Layer Composition in 10 mM MES Buffer at pH = 5.5

| Component | Concentration (mg/mL) |
| --- | --- |
| KRT | 28 |
| Albumin | 8 |
| NAD$^+$ or NADP$^+$ | 8 |
| PEGDGE 400 | 4 |

Various sensors were prepared using as provided above in Example 1 using KRTs obtained from Codexis®, headquartered in Redwood City, CA The Codexis® Enzyme Code ("Codexis® Ref.") for each of the 24 KRTs tested, as well as their respective co-factor (NAD+ or NADP+) are provided in Table 3, and identified as samples A1-A24 ("ID") hereinafter.

TABLE 3

| ID | Codexis ® Ref. | Co-factor |
| --- | --- | --- |
| A1 | KRED-P1-A04 | NAD(P)$^+$ |
| A2 | KRED-P1-A12 | NAD(P)$^+$ |
| A3 | KRED-P1-B02 | NAD(P)$^+$ |
| A4 | KRED-P1-B05 | NAD(P)$^+$ |
| A5 | KRED-P1-B10 | NAD(P)$^+$ |
| A6 | KRED-P1-B12 | NAD(P)$^+$ |
| A7 | KRED-P1-C01 | NAD(P)$^+$ |
| A8 | KRED-P1-H08 | NAD(P)$^+$ |
| A9 | KRED-P2-B02 | NAD(P)$^+$ |
| A10 | KRED-P2-C02 | NAD(P)$^+$ |
| A11 | KRED-P2-C11 | NAD(P)$^+$ |

TABLE 3-continued

| ID | Codexis ® Ref. | Co-factor |
| --- | --- | --- |
| A12 | KRED-P2-D03 | NAD(P)$^+$ |
| A13 | KRED-P2-D11 | NAD(P)$^+$ |
| A14 | KRED-P2-D12 | NAD(P)$^+$ |
| A15 | KRED-P2-G03 | NAD(P)$^+$ |
| A16 | KRED-P2-H07 | NAD(P)$^+$ |
| A17 | KRED-P3-B03 | NAD(P)$^+$ |
| A18 | KRED-P3-G09 | NAD(P)$^+$ |
| A19 | KRED-P3-H12 | NAD(P)$^+$ |
| A20 | KRED-101 | NAD(P)$^+$ |
| A21 | KRED-119 | NAD(P)$^+$ |
| A22 | KRED-130 | NAD(P)$^+$ |
| A23 | KRED-NADH-101 | NAD$^+$ |
| A24 | DRED-NADH-110 | NAD$^+$ |

Figure 5A:
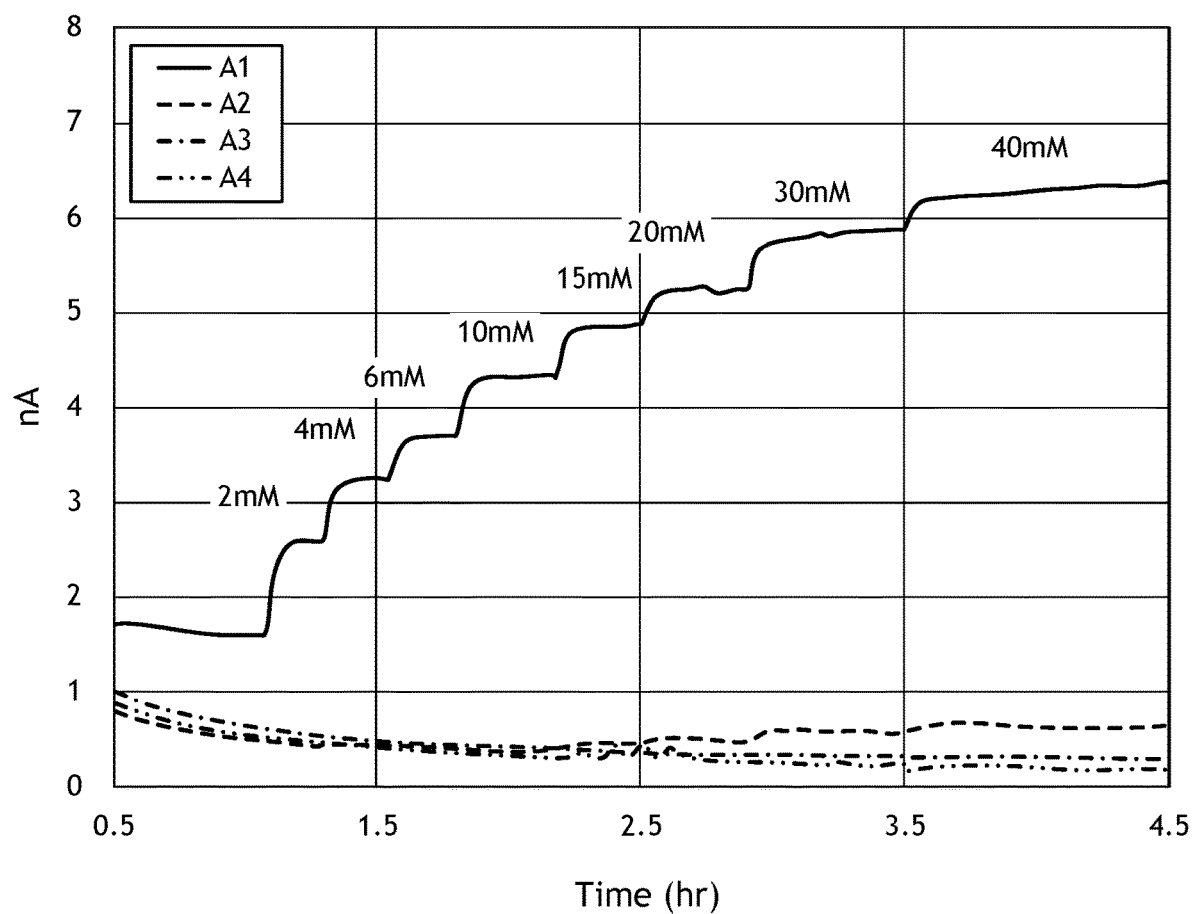
FIGS. 5A-5D show a graphical representation of the response of various KRT-comprising sensors to various ethanol concentrations.
Figure 5B:
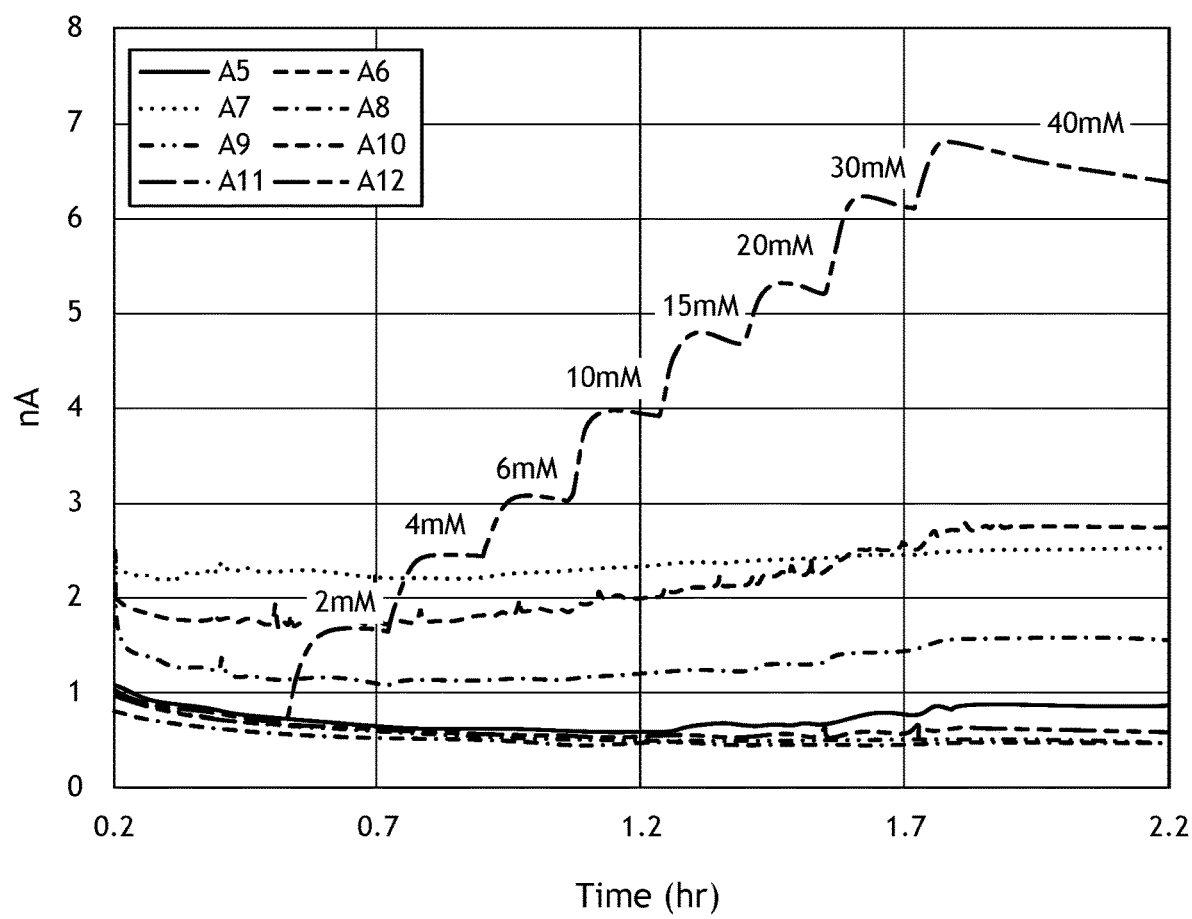
Figure 5C:
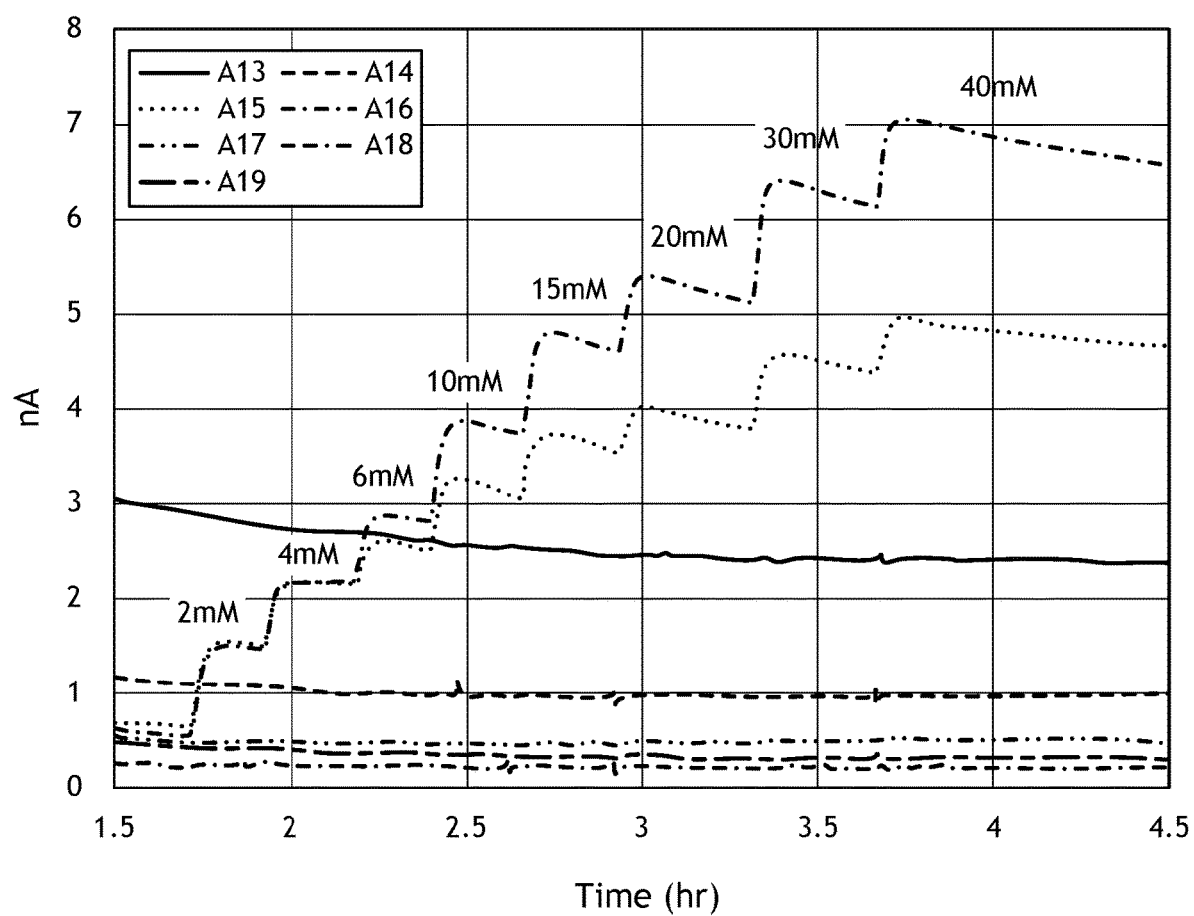
Figure 5D:
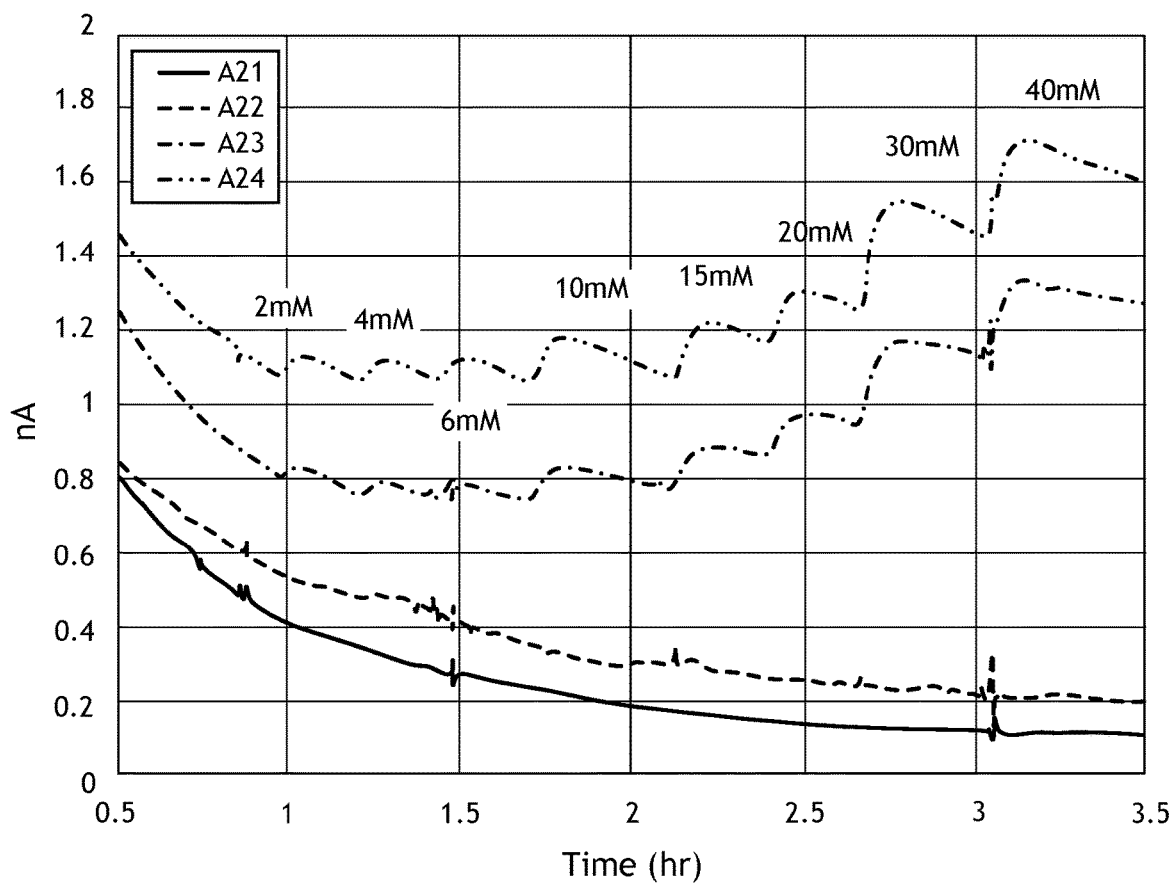
Figure 5E:
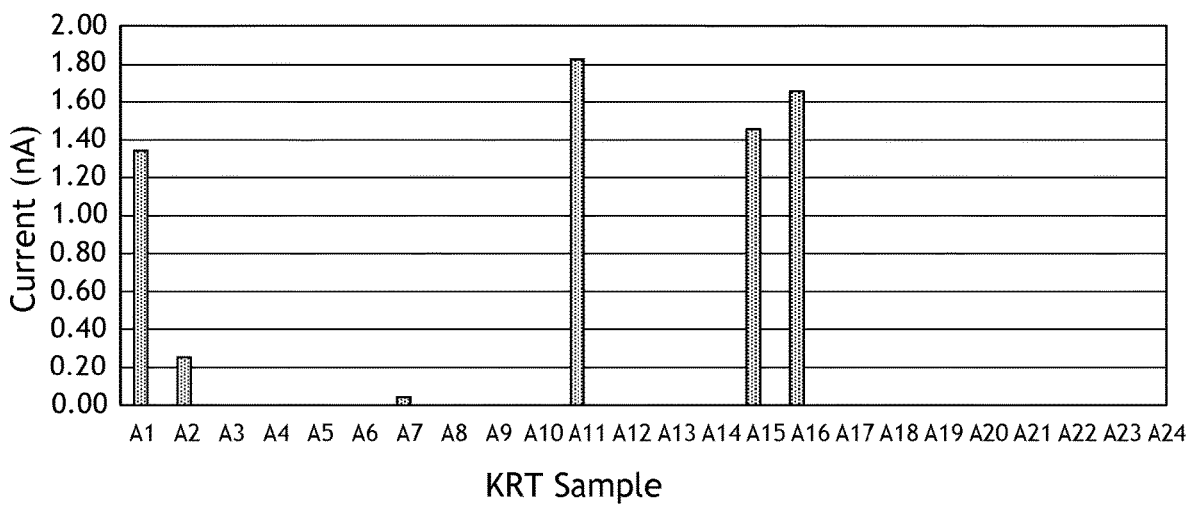
FIG. 5E shows a graphical representation of the response of four of the KRT-comprising sensors from FIGS. 5A-5C at 4 mM ethanol, showing the change (Δ) in current response from baseline (no EtOH exposure) to 4 mM ethanol.

Beaker Calibration of A1-A24 Sensors. Alcohol sensing analyses of the sensors comprising A1-A24 KRTs prepared according to Example 1 were conducted by immersing the electrode in a 100 mM PBS buffer solution at 33° C. and varying concentrations of ethanol (2, 4, 6, 10, 15, 20, 30, and 40 mM ethanol). FIGS. 5A-5D show the response of each of A1-A24. As shown, various of the KRT sensors were non-responsive, only minimally responsive, or inconsistently responsive to the ethanol. FIG. 5E is a static view of the beaker calibration at 4 mM ethanol showing the change (Δ) in current response from baseline (no EtOH exposure) to 4 mM ethanol. As shown, at 4 mM of ethanol, the Δ in sensor response prepared using KRT IDs A1, A11, A15, and A16 demonstrated substantial response to ethanol, which is also reflected at various other ethanol concentrations in FIGS. 5A-5C, and thus likely candidates for use in alcohol sensing. Accordingly, KRT IDs A1, A11, A15, and A16 were further evaluated.

Example 2

Example 2 evaluates the function of an alcohol sensor comprising KRT IDs A1, A11, A15, and A16 compared to a control alcohol dehydrogenase active area system.

Alcohol Sensor Preparation. Experimental A1, A11, A15, and A16 KRT alcohol-responsive active areas were prepared using a single-layer active area system and compared to a control ADH-comprising sensor. The ADH was obtained from Sigma-Aldrich Corp., headquartered in St. Louis, MO, having product number A3263. The ADC control utilizes the NAD$^+$ co-factor. The active area was coated onto a carbon working electrode in a single layer composition (Table 4 below). Following deposition of the active area, the active area was cured overnight at RT. Thereafter, a PVP membrane was applied to the working electrode using a membrane coating solution comprising 4 mL of 100 mg/mL polyvinylpyridine and 100 μl of 100 mg/mL PEGDGE 400. The membrane was deposited over the active area (3×5 mm/second dipping) and allowed to cure overnight at RT, followed by 48 hours at 56° C. in desiccated vials.

TABLE 4

Example 2 Active Area Composition in 10 mM MES Buffer at pH = 5.5

| Component | Concentration (mg/mL) |
| --- | --- |
| KRT or ADH | 16 |
| Diaphorase | 4 |
| Albumin | 8 |
| NAD$^+$ or NAD(P)$^+$ | 8 |

TABLE 4-continued

Example 2 Active Area Composition
in 10 mM MES Buffer at pH = 5.5

| Component | Concentration (mg/mL) |
|---|---|
| Osmium Polymer Complex | 8 |
| PEGDGE 400 | 4 |

Figure 6A:
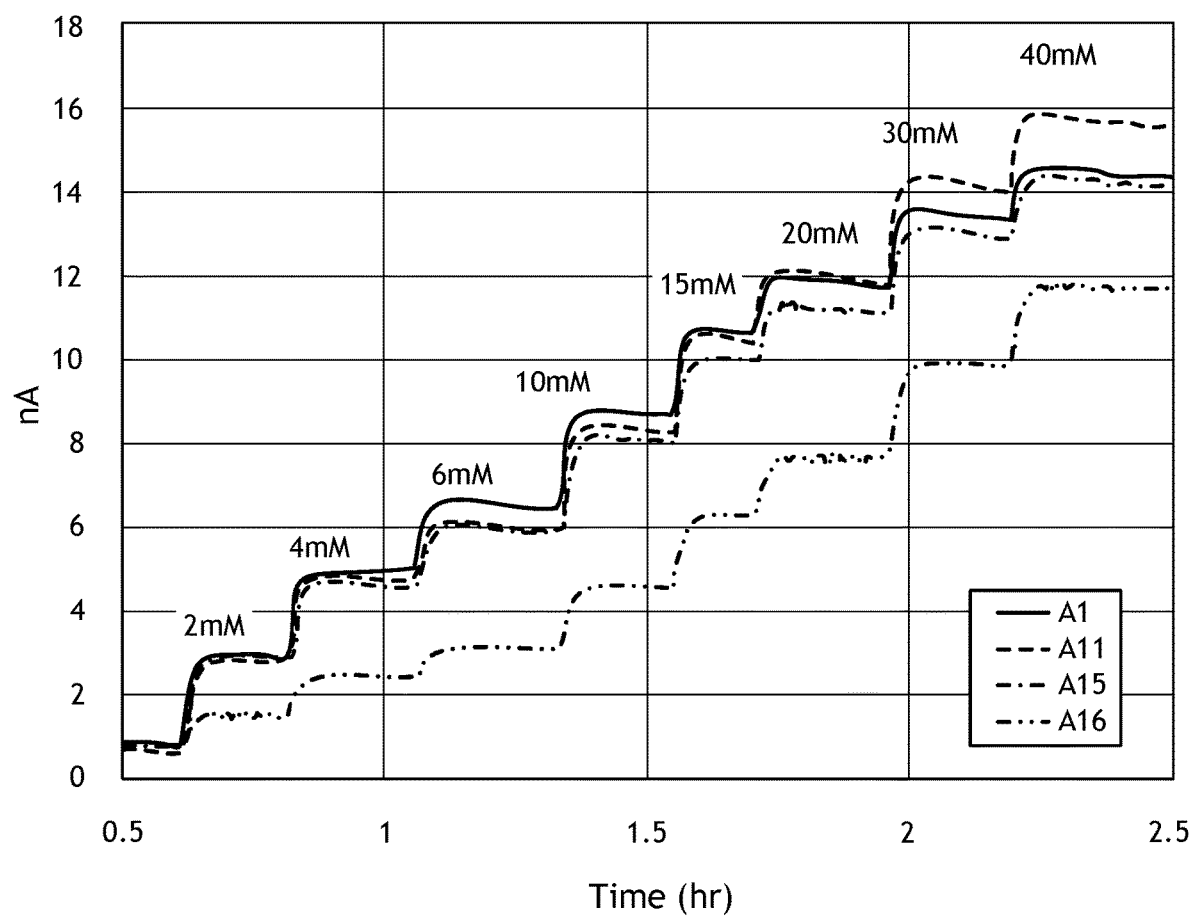
FIG. 6A shows a graphical representation of the response of various KRT-comprising sensors to various ethanol concentrations.
Figure 6B:
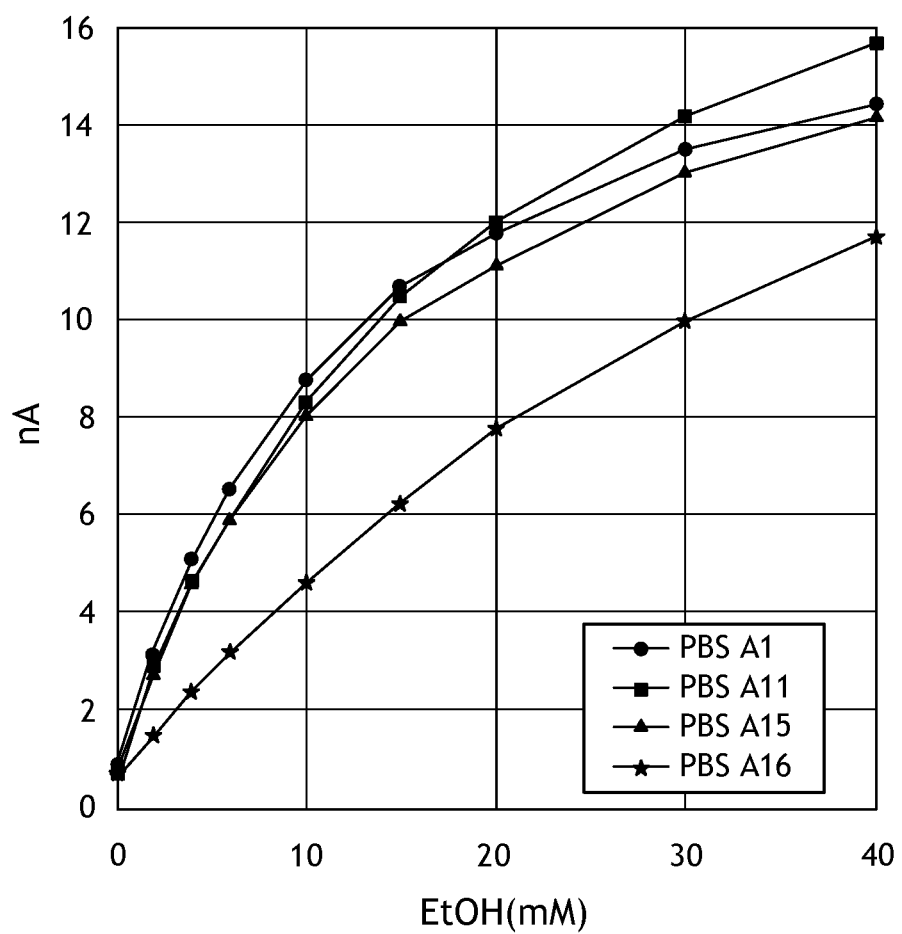
FIG. 6B shows the linear sensitivity response of the ethanol concentrations measured in FIG. 6A.

Beaker Calibration of A1-A24 Sensors. Alcohol sensing analyses of the sensors comprising A1, A11, A15, and A16 KRTs prepared according to Example 2 were conducted by immersing the electrode in a 100 mM PBS buffer solution at RT and varying concentrations of ethanol (2, 4, 6, 10, 15, 20, 30, and 40 mM ethanol). FIG. 6A shows the response of each of A1, A11, A15, and A16. As shown, each of the KRTs demonstrate a measurable response to increasing ethanol concentrations. FIG. 6B shows the linear sensitivity response of the A1, A11, A25, and A16 KRT sensors based on the beaker calibration, demonstrating a positive driving force, particularly with respect to A1, A11, and A15.

Figure 6C:
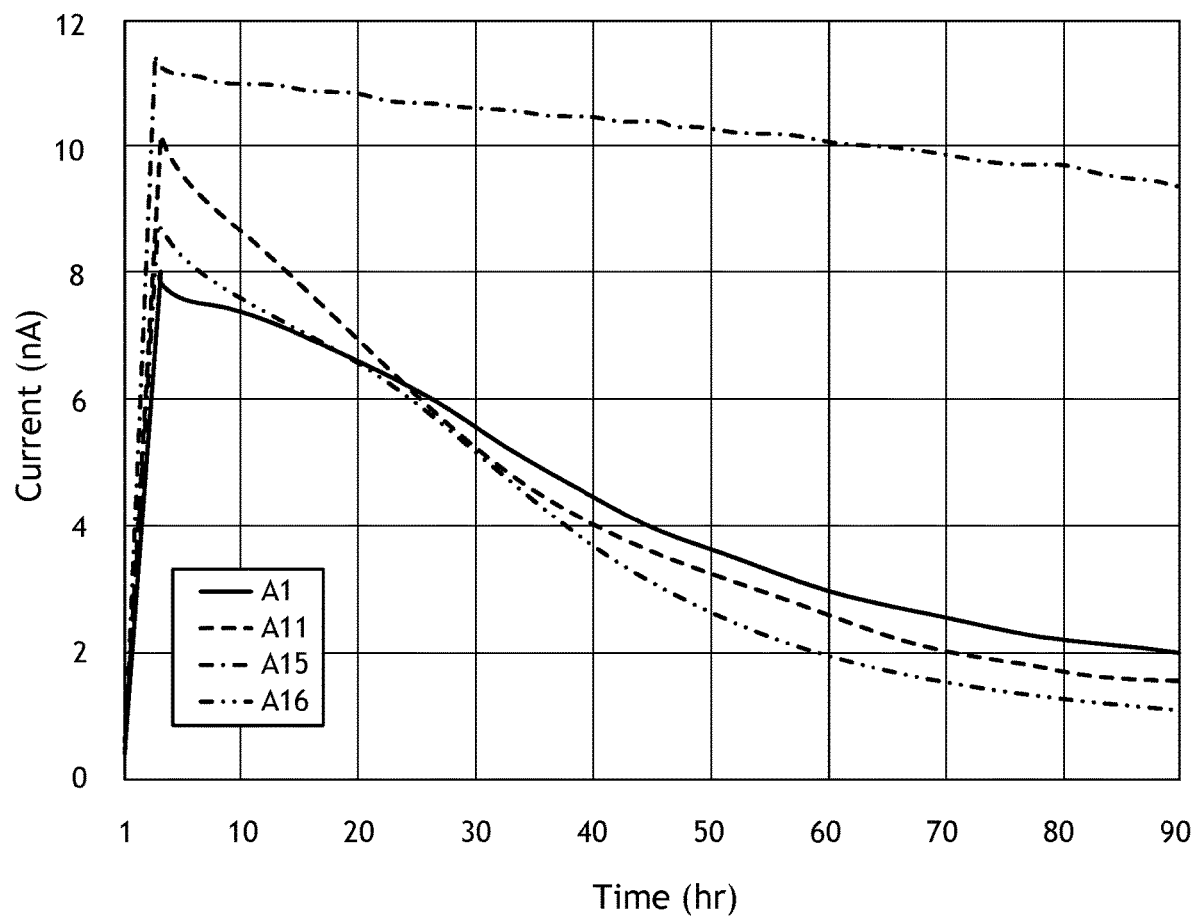
FIG. 6C shows a graphical representation of the stability response of the various KRT-comprising sensors of FIG. 6A.

Beaker Stability. The beaker stability (long-term stability) of the A1, A11, A15, and A16 sensors of Example 2 were evaluated in 30 mM EtOH in 100 mM PBS at 52° C. The results, shown in FIG. 6C, demonstrate that after 4 days, each of the signals experience sensor drop (decreased stability for detecting alcohol) of different rates, as provided in Table 5. Notably, the signal drop of the A15 sensor is substantially less than that of the other tested KRT sensors.

TABLE 5

Example 2 Signal Drop in 4 Days

| Sensor KRT ID | % Drop |
|---|---|
| A1 | −75% |
| A11 | −83% |
| A15 | −16% |
| A16 | −87% |

Figure 7:
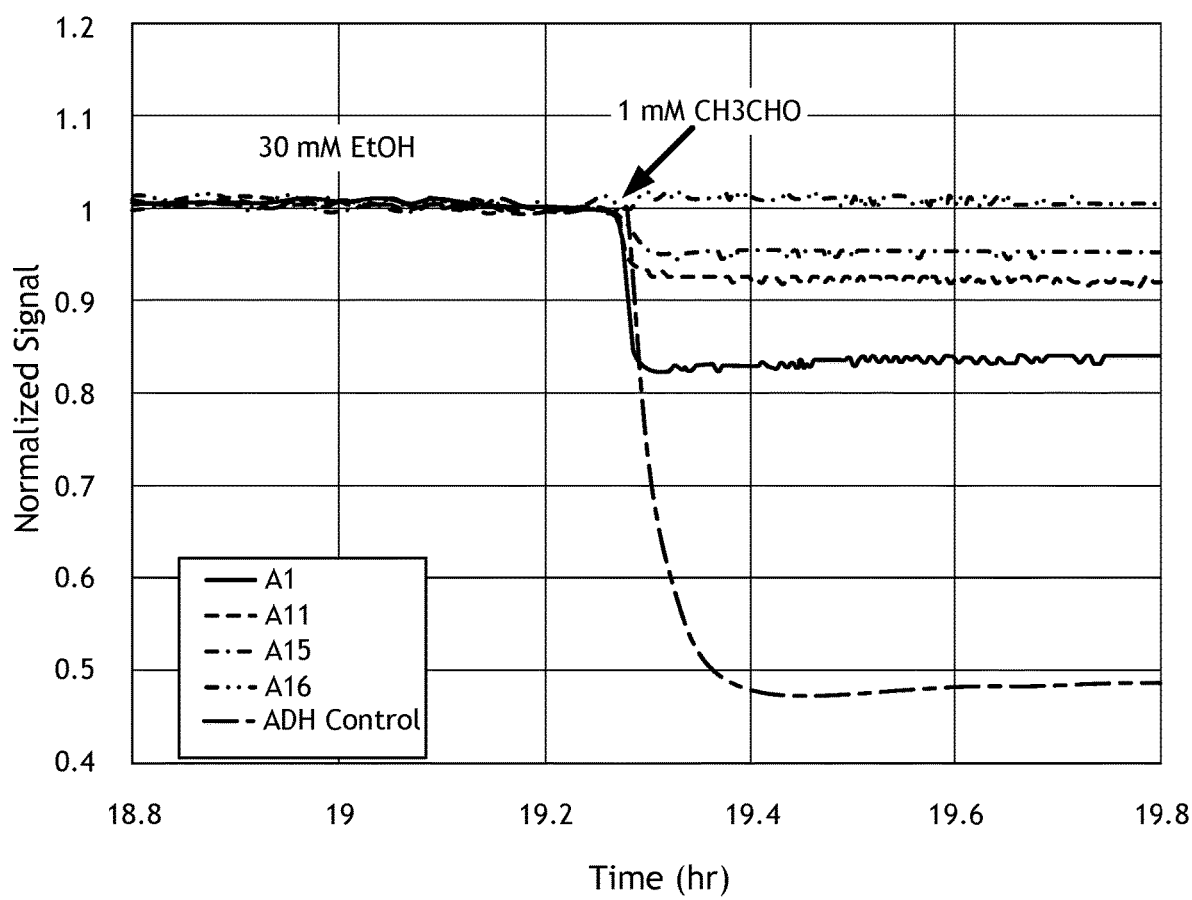
FIG. 7 shows a graphical representation of the stability response of various KRT-comprising sensors and an ADH control sensor to aldehyde exposure.

Aldehyde Inhibition. The aldehyde inhibition (e.g., acetaldehyde inhibition discussed herein above) on the performance of the A1, A11, A15, and A16 sensors of Example 2 were compared to the ADH control sensor of Example 2. The sensors were incubated over time in 30 mM EtOH in 100 mM PBS at 33° C., and thereafter spiked with 1 mM of acetaldehyde (at approximately 19.3 hours). The normalized signal results are shown in FIG. 7. As shown, the effect of aldehyde inhibition was none or negligible for the A15 and A16 sensors up to approximately 20 hours; the A1 and A11 sensors showed slightly greater inhibition; and the ADH control sensor exhibited substantial inhibition. The percentage drop in signal due to aldehyde inhibition for the sensors tested is provided in Table 6.

TABLE 6

Example 2 Aldehyde Inhibition

| Sensor KRT ID or Control | % Drop |
|---|---|
| A1 | −16% |
| A11 | −8% |
| A15 | −5% |
| A16 | −1% |
| ADH Control | −51% |

Example 3

Figure 8:
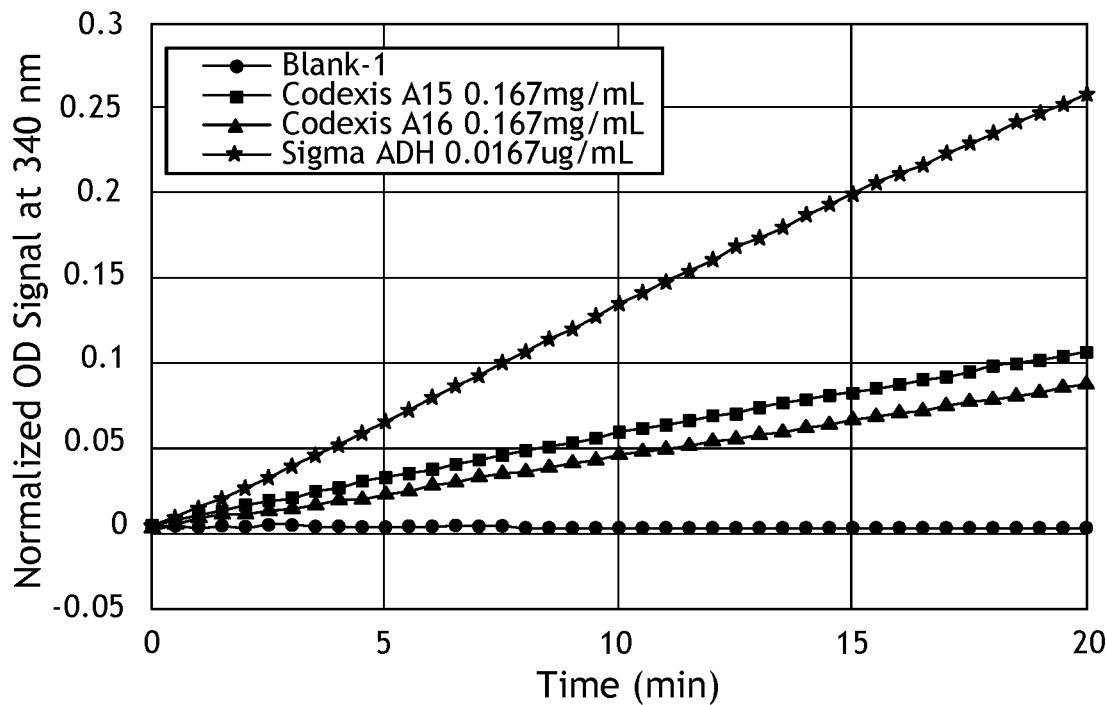
FIG. 8 shows a graphical representation of the results of a kinetics assay of various KRTs compared to ADH control.

A standard kinetics assay performed at RT was run for KRT IDs A15 and A16, and compared to ADH control (ADH described in Example 2 above). The co-factor $NAD^+$ (or $NADP^+$) was used in the reaction and the optical absorption ("OD") at 340 nm of the reduced NADH (or NADPH) measured. The concentration of A15 and A16 used in the kinetic assay was 0.167 mg/mL and the concentration of ADH control used in the kinetic assay was 0.0167 μg/mL (orders of magnitude less than A15 and A16), both in PBS buffer. The results of the kinetics assay are graphically shown in FIG. 8. The numeric results are provided in Table 7. Notably, the substantially reduced amount of ADH control enzyme, compared to the A15 and A16 KRT enzymes nevertheless resulted in roughly 260% greater kinetic activity but A15 and A16 shows significantly greater resistance to aldehyde inhibition (see FIG. 7).

TABLE 7

| | ADH | A15 | A16 |
|---|---|---|---|
| OD/min | 0.0132 | 0.0051 | 0.0043 |
| (OD/min)/(mg/mL) | 790 | 0.031 | 0.026 |
| units/mg activity | 288 | 0.011 | 0.009 |

Example 4

Figure 9A:
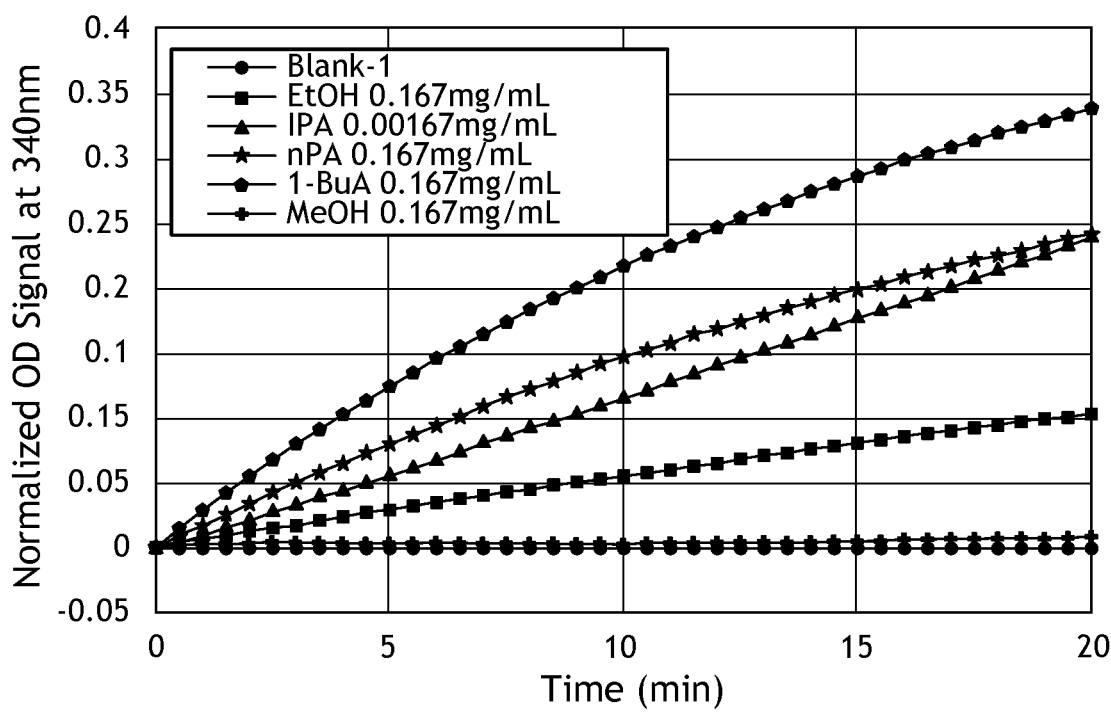
FIGS. 9A and 9B show graphical representations of the results of a kinetics assay of two KRTs in different alcohol types.
Figure 9B:
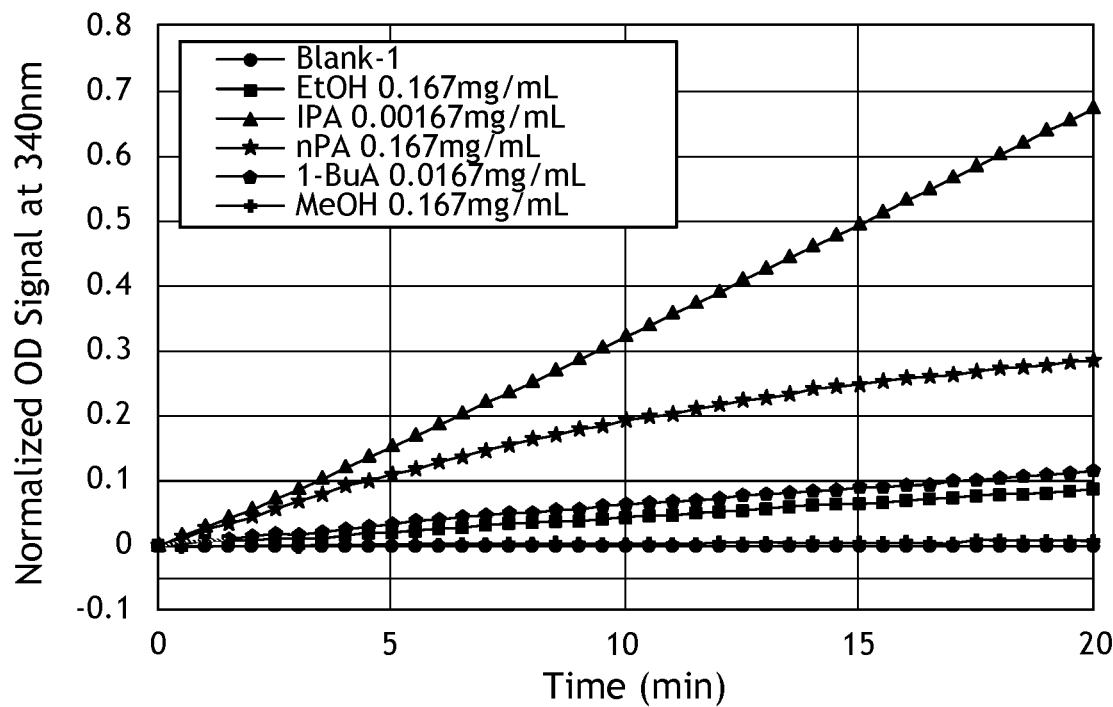

A standard kinetics assay performed at RT was run for KRT IDs A15 and A16, each in various types of alcohol, and compared to ADH control (ADH described in Example 2 above). The co-factor $NAD(P)^+$ was used in the reaction and the optical absorption ("OD") at 340 nm of the reduced NAD(P)H measured. Testing of A15 and A16 in the kinetics assay is shown in FIGS. 9A and 9B and was performed in ethanol (EtOH), isopropyl alcohol (IPA), propanol (nPA), butanol (1-BuA), and methanol (MeOH). The "Blank" excluded the KRT enzyme. The results of the KRT kinetics assay are graphically shown in FIGS. 9A and 9B, in which 9A pertains to A15 and 9B pertains to A16. The numeric results are provided in Table 8, including those measured for the ADH control (not otherwise represented in graphical form). Notably, the KRTs exhibited substantially greater enzymatic activity in the IPA compared to the ADH control, further demonstrating that KRT sensors described herein may be used for alcohols other than primary alcohols.

TABLE 8

| Units/mg Activity | ADH | A15 | A16 |
|---|---|---|---|
| MeOH | 0.000 | 0.001 | 0.000 |
| EtOH | 288.000 | 0.012 | 0.009 |
| IPA | 0.709 | 2.553 | 7.091 |
| nPA | 4.211 | 0.032 | 0.042 |
| 1-BuA | 1.309 | 0.047 | 0.131 |

Example 5

In this Example, KRT-comprising sensors having additional polymers and/or crosslinkers compared in addition to the composition elements of Example 2 were evaluated.

Figure 10A:
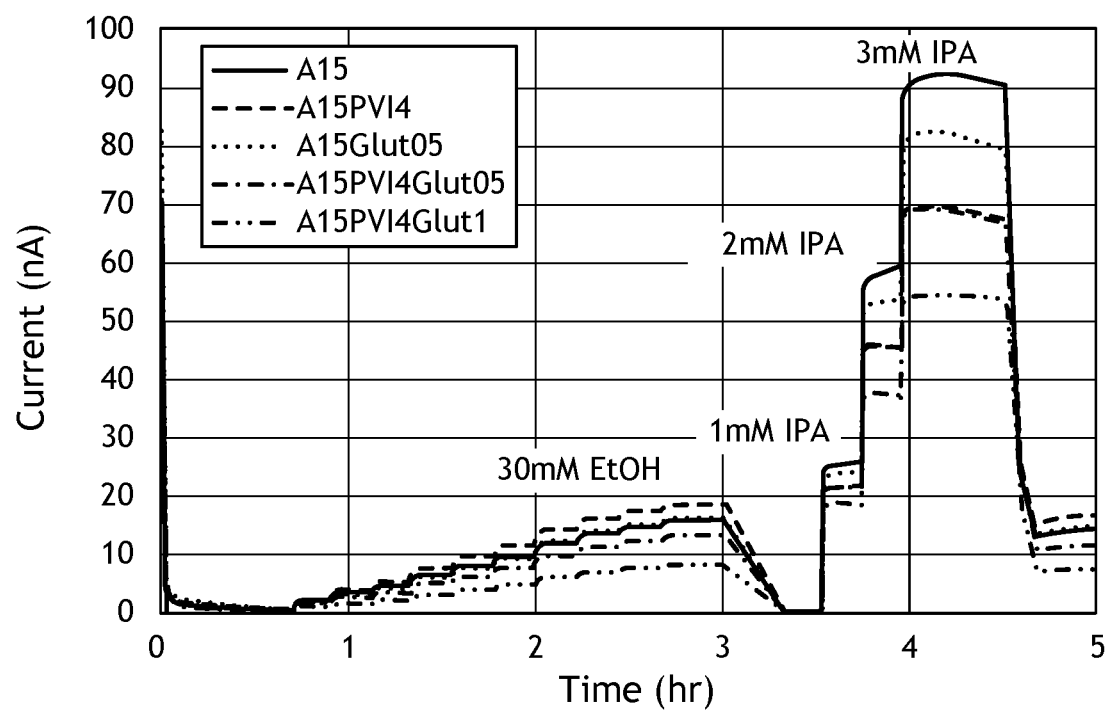
FIGS. 10A and 10B show graphical representations of the response of two KRT-comprising sensors of various compositions to IPA.
Figure 10B:
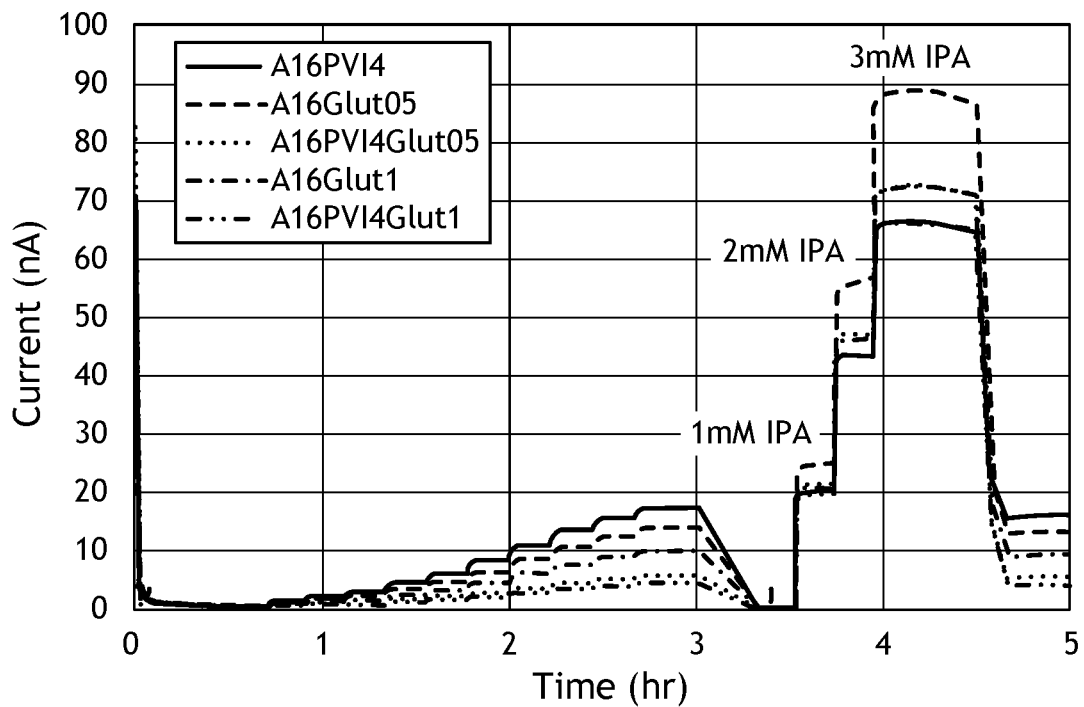

IPA Response. In response to the results in Example 4, the effect of IPA on A15 and A16 were further exampled. A15 and A16 sensors were prepared according to Example 2, in which one or more additional polymers or crosslinkers was added to the active area composition in some instances. The additional polymer was poly(1-vinyl imidazole) ("PVI") and the additional crosslinker was glutaraldehyde ("Glut"). The current response of the sensors was initially measured in 30 mM EtOH in 100 mM PBS buffer for approximately 3.5 hours at 33° C. and thereafter spiked (buffer replaced and IPA added) with increasing concentrations of IPA (1, 2, and 3 mM IPA). The results are shown in FIGS. 10A and 10B, in which 10A pertains to A15 and 10B pertains to A16. The additional polymer and/or crosslinker for each sensor tested is shown in Table 9 based on the legend references of FIGS. 10A and 10B, represented as mg/mL of total active area and the "—" symbol indicates that the component was not added.

TABLE 9

| FIG. 10A/10B Legend Reference | PVI (mg/mL) | Glut (mg/mL) |
| --- | --- | --- |
| A15 | — | — |
| A15PVI4 | 4 | — |
| A15Glut05 | — | 0.5 |
| A15PVI4Glut05 | 4 | 0.5 |
| A15PVI4Glut1 | 4 | 1 |
| A16PVI4 | 4 | — |
| A16Glut05 | — | 0.5 |
| A16PVI4Glut05 | 4 | 0.5 |
| A16Glut1 | — | 1 |
| A16PVI4Glut1 | 4 | 1 |

As shown in FIGS. 10A and 10B, the response to 1_mM IPA is approximately 12 times greater than the response to 30 mM EtOH. Further as shown in FIG. 10A, the A15 sensors comprising glutaraldehyde crosslinker exhibited greater sensitivity to IPA in generally, with the A15 sensor comprising only glutaraldehyde (and no PVI) exhibiting the most sensitivity. A similar result is shown in FIG. 10B with reference to the A16 sensors; however, the lesser concentration of glutaraldehyde (0.5 mg/mL) compared to the higher concentration of glutaraldehyde (1 mg/mL) exhibited greater sensitivity to IPA.

Figure 11A:
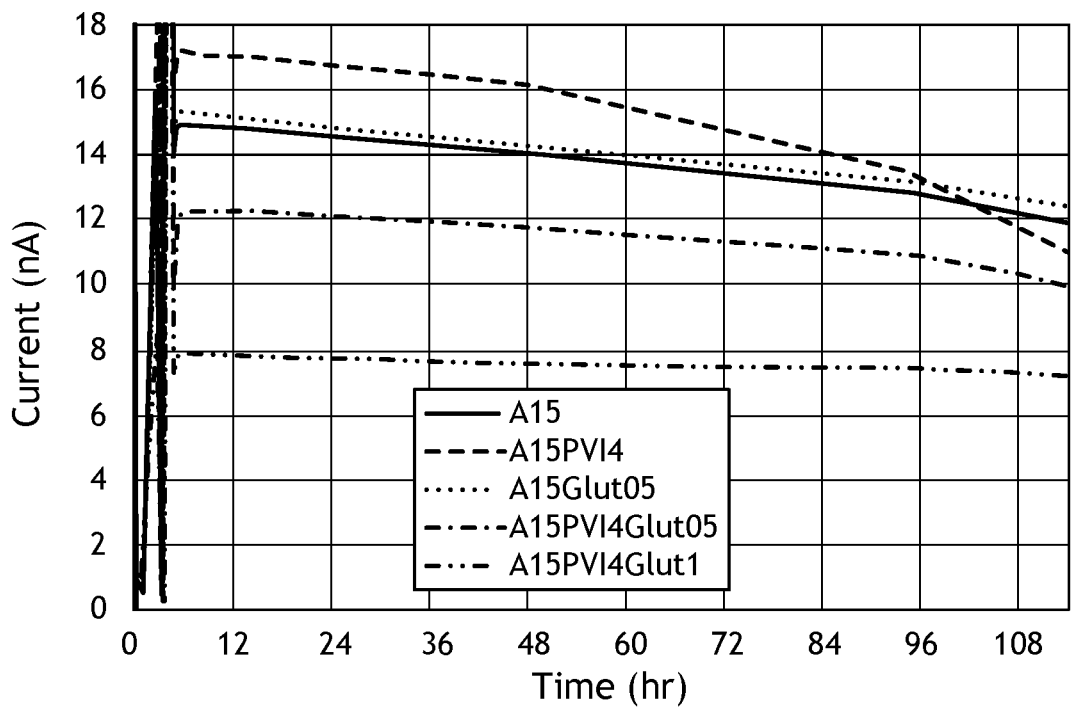
FIGS. 11A and 11B show graphical representations of the stability response of various KRT-comprising sensors having different additional polymer and crosslinker compositions.
Figure 11B:
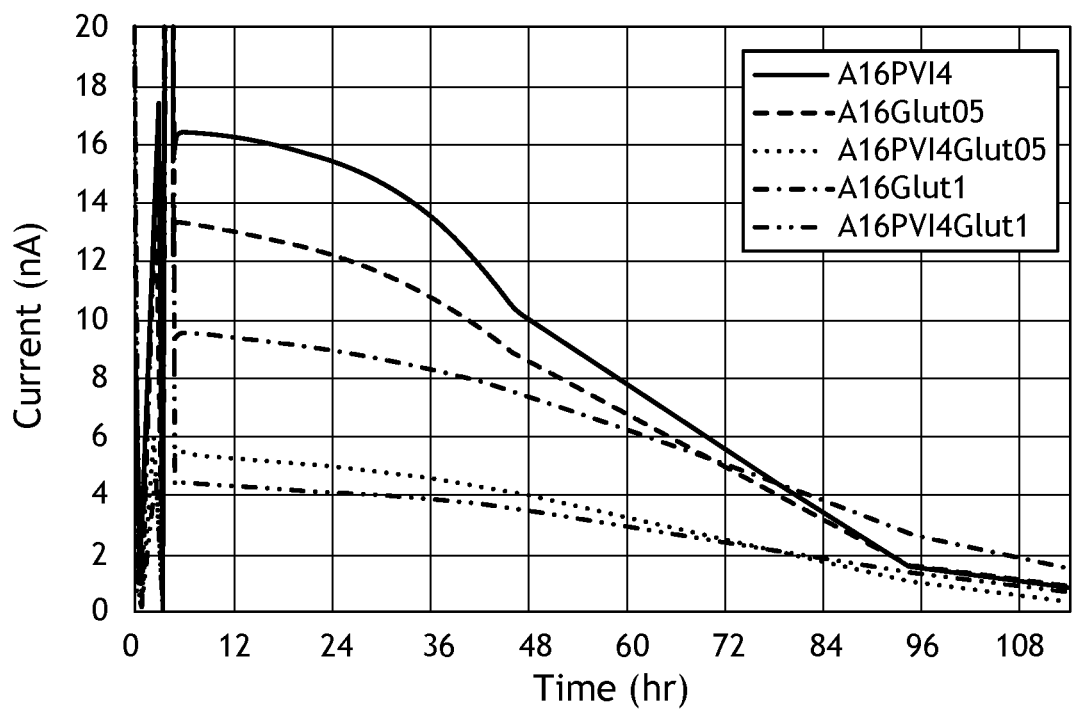

Beaker Stability. The beaker stability (long-term stability) of the A15 and A16 sensors of Example 5 were evaluated in 30 mM EtOH in 100 mM PBS at 33° C. The results are shown in FIGS. 11A and 11B, in which 11A pertains to A15 and 11B pertains to A16. As shown, the stability of the A15 sensors is greater than the stability of the A16 sensors. Further, the stability of the A15 sensors comprising additional glutaraldehyde crosslinkers outperform those of the other A15 compositions. Active area precipitate was observed, however, in the A15PVI4Glut05 and A15PVI4Glut1 samples; more particularly, the active area appeared cloudy when both PVI and glutaraldehyde were included. Table 10 provides the numerical sensor drop out experienced by the A15 sensors in 5 days.

TABLE 10

Example 5 Signal Drop in 4 Days

| Sensor KRT ID | % Drop |
| --- | --- |
| A15 | −24% |
| A15PVI4 | −37% |
| A15Glut05 | −18% |
| A15PVI4Glut05 | −15% |
| A15PVI4Glut1 | −8.5% |

Example 6

In this Example, a KRT-comprising sensor having additional polymer was compared to an ADH control sensor.

Figure 12A:
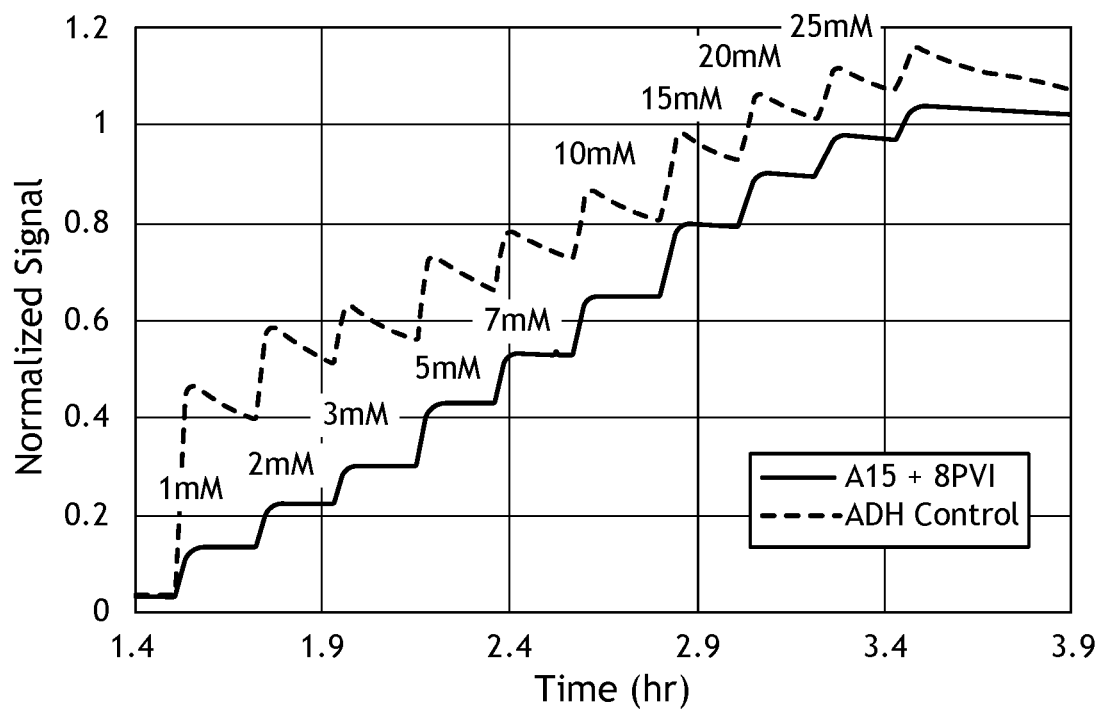
FIG. 12A shows a graphical representation of the response of a particular KRT-comprising sensor comprising particular polymer composition to comprising various ethanol concentrations.
Figure 12B:
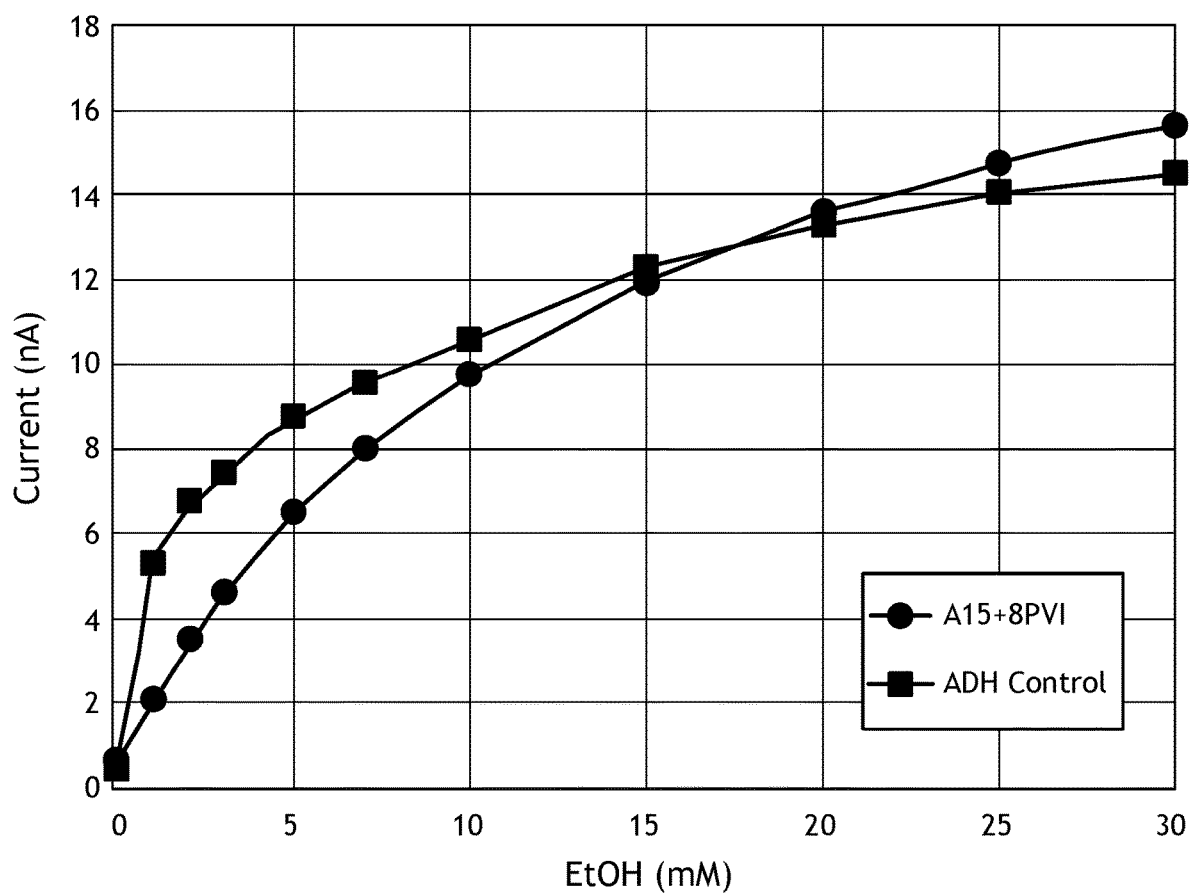
FIG. 12B shows the linear sensitivity response of the ethanol concentrations measured in FIG. 12A. ADH Control means alcohol dehydrogenase (ADH) from signal.

Beaker Calibration. Alcohol sensing analysis of an A15 sensor prepared according to Example 2, further comprising 8 mg/mL of PVI in the active area, was tested to determine its response to various concentrations of EtOH (1, 2, 3, 5, 7, 10, 15, 20, 25, and 30 mM EtOH) in 100 mM PBS buffer at 33° C. The KRT A15 sensor was compared to an ADH control sensor prepared according to Example 2. FIG. 12A shows the normalized signal response of each of the A15 sensor comprising the additional PVI polymer (labeled A15+8PVI) and ADH control sensor. As shown, the A15 sensor exhibits greater ethanol sensitivity (i.e., the loss of signal is significantly greater in the ADH control after each greater concentration of EtOH), as further shown in FIG. 12B, which shows the linear sensitivity response of the two tested sensors.

Figure 13:
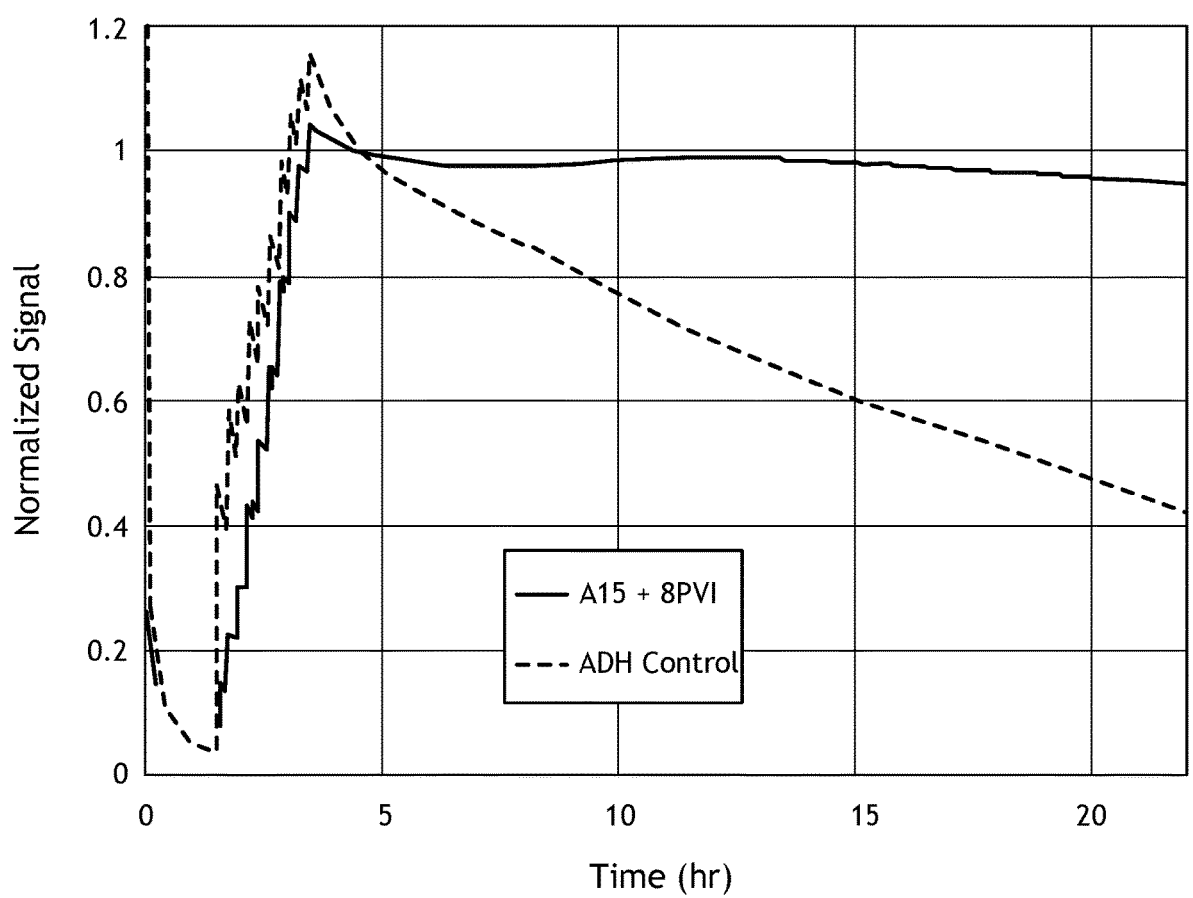
FIG. 13 shows a graphical representation of the stability response of a particular KRT-comprising sensor comprising particular polymer composition.

Beaker Stability. The beaker stability (long-term stability) of the A15 and ADH control sensors of Example 6 were evaluated in 30 mM EtOH in 100 mM PBS at 33° C. The results, shown in FIG. 13, demonstrate that the stability of the KRT A15 sensor is significantly better compared to the ADH control sensor.

Example 7

Figure 14:
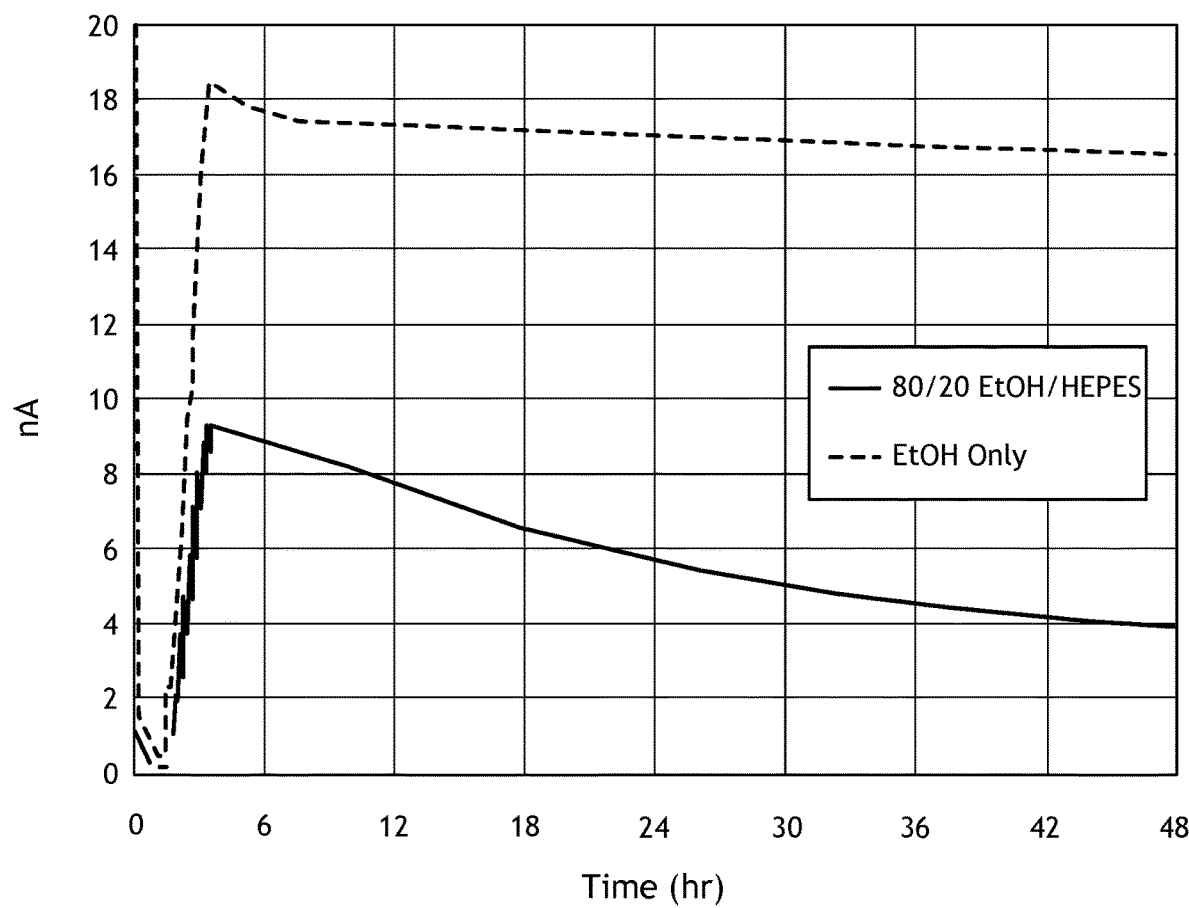
FIG. 14 shows a graphical representation of the stability response of a particular KRT-comprising sensor having a dipped membrane in two different solvents.

The beaker stability (long-term stability) of an A15 sensor prepared according to Example 2 was evaluated in two different membrane solvents, one comprising EtOH and the second comprising and 80:20 ratio of EtOH and HEPES buffer. The results are shown in FIG. 14 and demonstrate that the stability of the sensor in only EtOH solvent demonstrated greater stability compared to the diluted EtOH solvent.

Example 8

Figure 15:
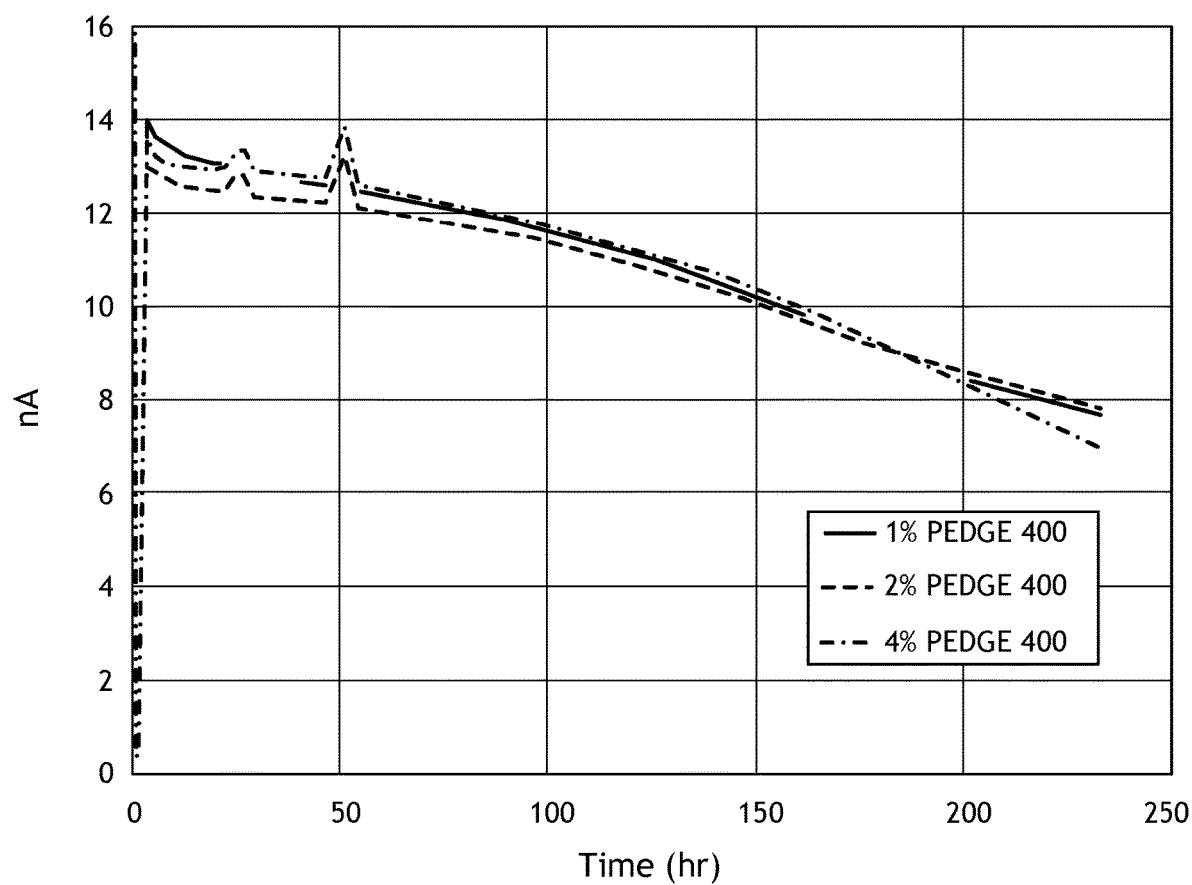
FIG. 15 shows a graphical representation of the stability response of various KRT-comprising sensors having different membrane compositions.

The beaker stability (long-term stability) of an analyte sensor comprising an active area prepared according to Example 2 with the addition of 1 mg/mL of glutaraldehyde were evaluated having differing membrane compositions (and different than that of Example 2) in 30 mM EtOH in 100 mM PBS buffer at 33° C. Three separate membrane compositions were prepared and coated upon the A15 active areas (further comprising the glutaraldehyde) comprising either 1%, 2%, or 4% of PEGDGE 400 in PVP. The results of the signal stability are shown in FIG. 15, which track each other closely. The short-term stability of the tested membranes is greater than the long-term based on the present composition. The numerical signal drop in 5 days and in 10 days are shown in Table 11.

TABLE 11

| Membrane | % Drop |
| --- | --- |
| Example 8 Signal Drop in 5 Days | |
| 1% PEDGE 400 | −14% |
| 2% PEDGE 400 | −13% |
| 4% PEDGE 400 | −13% |
| Example 8 Signal Drop in 10 Days | |
| 1% PEDGE 400 | −41% |
| 2% PEDGE 400 | −37% |
| 4% PEDGE 400 | −46% |

Example 9

Figure 16:
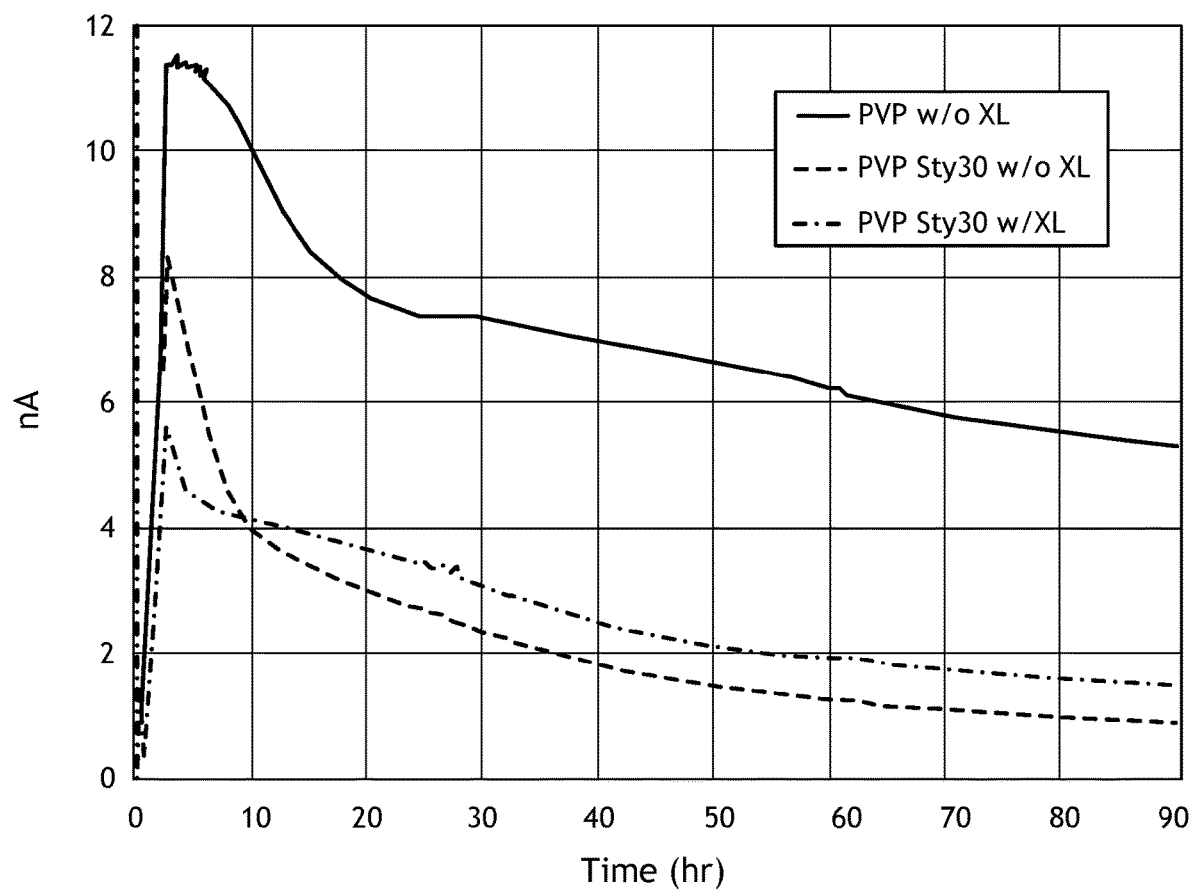
FIG. 16 shows a graphical representation of the stability response of various KRT-comprising sensors having different membrane and crosslinker compositions.

The beaker stability (long-term stability) of an analyte sensor comprising an active area prepared according to Example 2 with the addition of 1 mg/mL of glutaraldehyde were evaluated having differing membrane compositions (and different than that of Example 2) in 30 mM EtOH in 100 mM PBS buffer at 33° C. Three separate membrane compositions were prepared and coated upon the A15 active areas (further comprising the glutaraldehyde) comprising either PVP without any crosslinker, polyvinylpyridine-co-styrene(30) (i.e., having 30% styrene) ("PVPSty30") without any crosslinker, and PVPSty30 with 4% crosslinker of PEGDGE 400. The results of the signal stability are shown in FIG. 16, illustrating the addition of the crosslinker does not appear to be a significant influence to KRT sensor stability.

In general, the embodiments of the present disclosure indicate that a concerted enzyme system comprising KRT enzymes may be viable as an alcohol sensor for detected alcohol levels of an individual, particularly in vivo (but may also be used for in vivo measurements). Of the tested KRTs in the present disclosure, KRT sensors comprising A15 show the greatest stability (beaker stability) and A16 shows the least product inhibition; and both have much higher specific activity to IPA than EtOH (e.g., 200× higher for A15 and 700× higher for A16).

Unless otherwise indicated, all numbers expressing quantities and the like in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating various features are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While various systems, tools and methods are described herein in terms of "comprising" various components or steps, the systems, tools and methods can also "consist essentially of" or "consist of" the various components and steps.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Therefore, the disclosed systems, tools and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems, tools and methods illustratively disclosed herein may suitably be practiced in the absence of any element that is not specifically disclosed herein and/or any optional element disclosed herein. While systems, tools and methods are described in terms of "comprising," "containing," or "including" various components or steps, the systems, tools and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

What is claimed is:

1. An analyte sensor comprising:
   a sensor tail comprising at least a working electrode; and
   at least one alcohol-responsive active area disposed upon a surface of the working electrode, the at least one alcohol-responsive active area comprising at least (i) ketoreductase, (ii) diaphorase, and (iii) a cofactor that is either oxidized nicotinamide adenine dinucleotide (NAD+) or oxidized nicotinamide adenine dinucleotide phosphate (NAD(P)+,
   wherein a reaction between the ketoreductase and diaphorase, mediated by the co-factor, generates a signal proportional to a concentration of alcohol,
   wherein the at least one alcohol-responsive active area comprises a polymer, and
   wherein the (i) ketoreductase and (ii) diaphorase are chemically bound to the polymer.

2. The analyte sensor of claim 1, wherein the ketoreductase is an aldo-ketoreductase.

3. The analyte sensor of claim 1, wherein the ketoreductase is KRED-P1-A04, KRED-P2-C11, KRED-P2-G03, or KRED-P2-H07.

4. The analyte sensor of claim 1, wherein a membrane is disposed upon the at least one alcohol-responsive active area.

5. The analyte sensor of claim 4, wherein the membrane is one of a polyvinyl pyridine, a polyvinylimidazone, or any copolymer thereof.

6. The analyte sensor of claim 1, wherein the at least one alcohol-responsive active area comprises an electron transfer agent.

7. The analyte sensor of claim 1, wherein the at least one alcohol-responsive active area comprises a stabilizer.

8. A method comprising:
   detecting a signal proportional to a concentration of alcohol using an analyte sensor, the analyte sensor comprising:
      a sensor tail comprising at least a working electrode, the sensor tail configured for implantation into a tissue; and
      at least one alcohol-responsive active area disposed upon a surface of the working electrode, the at least one alcohol-responsive active area comprising at least (i) ketoreductase, (ii) diaphorase, and (iii) a cofactor that is either oxidized nicotinamide adenine dinucleotide (NAD+) or oxidized nicotinamide adenine dinucleotide phosphate (NAD(P)+,
   wherein a reaction between the ketoreductase and diaphorase, mediated by the co-factor, generates a signal proportional to a concentration of alcohol,
   wherein the at least one alcohol-responsive active area comprises a polymer, and
   wherein the (i) ketoreductase and (ii) diaphorase are chemically bound to the polymer.

9. The method of claim 8, wherein the ketoreductase is an aldo-ketoreductase.

10. The method of claim 8, wherein the ketoreductase is KRED-P1-A04, KRED-P2-C11, KRED-P2-G03, or KRED-P2-H07.

11. The method of claim 8, wherein a membrane is disposed upon the at least one alcohol-responsive active area.

12. The method of claim 11, wherein the membrane is one of a polyvinyl pyridine, a polyvinylimidazone, or any copolymer thereof.

13. The method of claim 8, wherein the at least one alcohol-responsive active area comprises an electron transfer agent.

14. The method of claim 8, wherein the at least one alcohol-responsive active area comprises a stabilizer.

15. The analyte sensor of claim 1, wherein the polymer in the at least one alcohol-responsive active area is a polyvinyl pyridine, a polyvinylimidazone, a copolymer thereof, or combination thereof.

16. The method of claim 8, wherein the polymer in the at least one alcohol-responsive active area is a polyvinyl pyridine, a polyvinylimidazone, a copolymer thereof, or combination thereof.

* * * * *